US008841070B2

(12) United States Patent
Harnack et al.

(10) Patent No.: US 8,841,070 B2
(45) Date of Patent: Sep. 23, 2014

(54) DEVICE FOR PROCESSING AN ANALYTE AND A METHOD OF PROCESSING AND/OR DETECTING AN ANALYTE USING SAID DEVICE

(75) Inventors: Oliver Harnack, Stuttgart (DE); Ingeborg Hospach, Stuttgart (DE); Claire Basquin, Munich (DE); Akio Yasuda, Suginami-ku (JP)

(73) Assignee: Sony Deutschland GmbH, Berlin (DE)

( * ) Notice: Subject to any disclaimer, the term of this patent is extended or adjusted under 35 U.S.C. 154(b) by 139 days.

(21) Appl. No.: 12/141,475

(22) Filed: Jun. 18, 2008

(65) Prior Publication Data
US 2009/0023146 A1    Jan. 22, 2009

(30) Foreign Application Priority Data

Jun. 22, 2007    (EP) .................................... 07012276

(51) Int. Cl.
| | | |
|---|---|---|
| C12Q 1/68 | (2006.01) | |
| C12M 1/36 | (2006.01) | |
| G01N 27/00 | (2006.01) | |
| B01L 3/00 | (2006.01) | |
| G01N 33/487 | (2006.01) | |

(52) U.S. Cl.
CPC ..... *B01L 3/502761* (2013.01); *G01N 33/48721* (2013.01); *B01L 2300/0896* (2013.01); *B01L 2400/043* (2013.01); *B01L 2200/0663* (2013.01); *B01L 2300/0636* (2013.01); *B01L 2200/027* (2013.01); *B01L 3/502715* (2013.01); *B01L 2400/0487* (2013.01); *B01L 2400/0415* (2013.01); *B01L 2200/10* (2013.01)
USPC ..... 435/6.1; 435/287.2; 435/287.3; 422/68.1; 422/82.01

(58) Field of Classification Search
None
See application file for complete search history.

(56) References Cited

U.S. PATENT DOCUMENTS

| | | | | |
|---|---|---|---|---|
| 5,674,743 | A * | 10/1997 | Ulmer | 435/287.2 |
| 5,795,782 | A * | 8/1998 | Church et al. | 436/2 |
| 5,872,003 | A * | 2/1999 | Koster | 435/283.1 |
| 6,274,337 | B1 | 8/2001 | Parce et al. | |
| 6,537,755 | B1 * | 3/2003 | Drmanac | 435/6 |
| 6,627,067 | B1 * | 9/2003 | Branton et al. | 205/778 |
| 6,696,022 | B1 * | 2/2004 | Chan et al. | 422/99 |
| 2003/0064400 | A1 | 4/2003 | Williams | |
| 2003/0186255 | A1 * | 10/2003 | Williams et al. | 435/6 |
| 2003/0187237 | A1 | 10/2003 | Chan et al. | |
| 2005/0186576 | A1 * | 8/2005 | Chan et al. | 435/6 |
| 2005/0221333 | A1 | 10/2005 | Sundararajan et al. | |
| 2006/0073489 | A1 * | 4/2006 | Li et al. | 435/6 |

FOREIGN PATENT DOCUMENTS

| | | |
|---|---|---|
| CN | 1681944 A | 10/2005 |
| WO | WO 02/099406 A2 | 12/2002 |

OTHER PUBLICATIONS

Craighead, H.G. "nanoelectromechanical Systems" Science, 2000, 290: 1532-1535.*
Office Action issued Aug. 7, 2013, in Chinese patent application No. 200810210378.9 (w/English translation).
Combined Chinese Office Action and Search Report issued Apr. 24, 2013, in Chinese Patent Application No. 200810210378.9 with English translation and English translation of category of cited documents.

* cited by examiner

*Primary Examiner* — Betty Forman
(74) *Attorney, Agent, or Firm* — Oblon, Spivak, McClelland, Maier & Neustadt, L.L.P.

(57) ABSTRACT

The present invention relates to a device for processing an analyte and to a method of processing and/or detecting an analyte using said device.

45 Claims, 22 Drawing Sheets

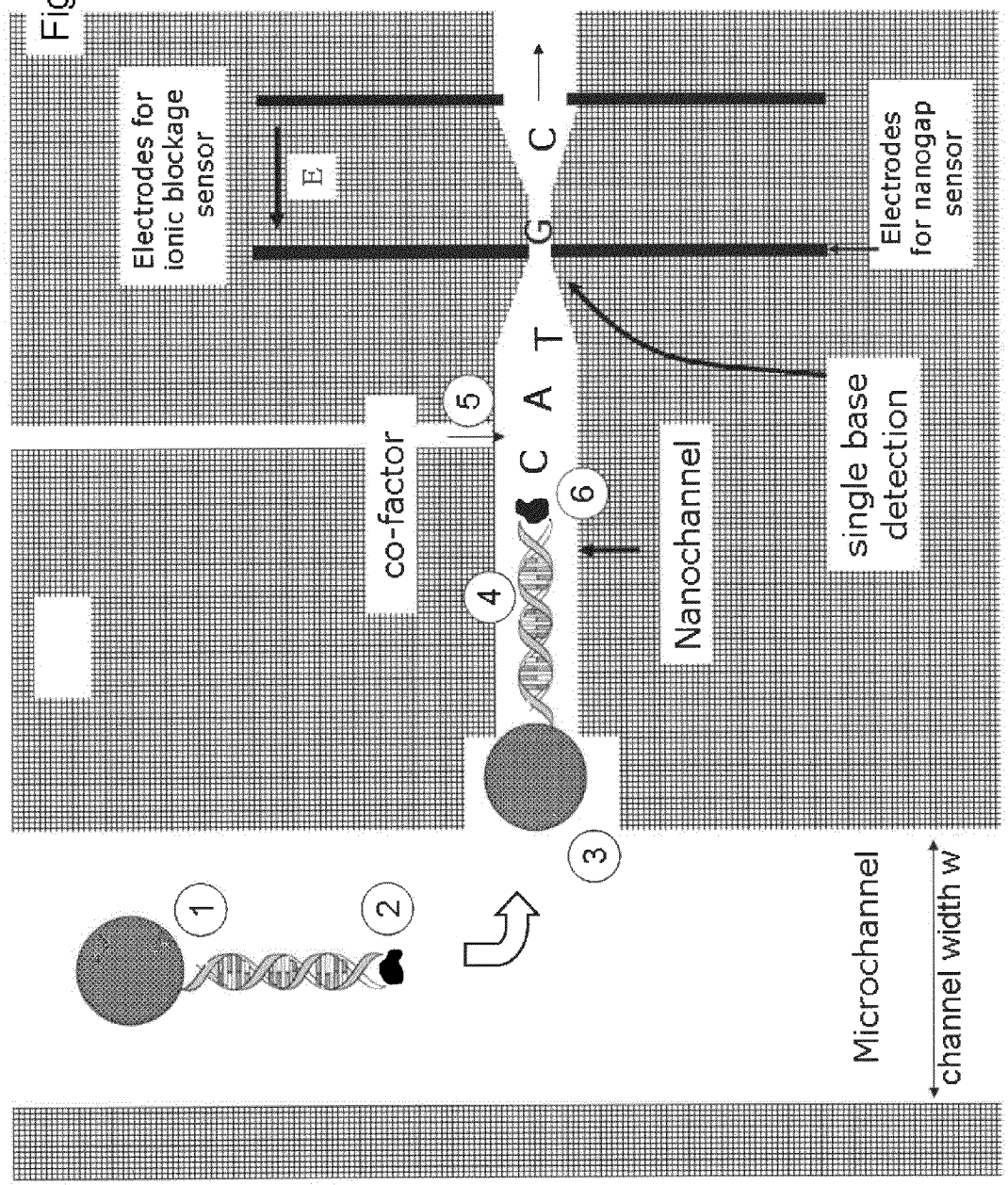

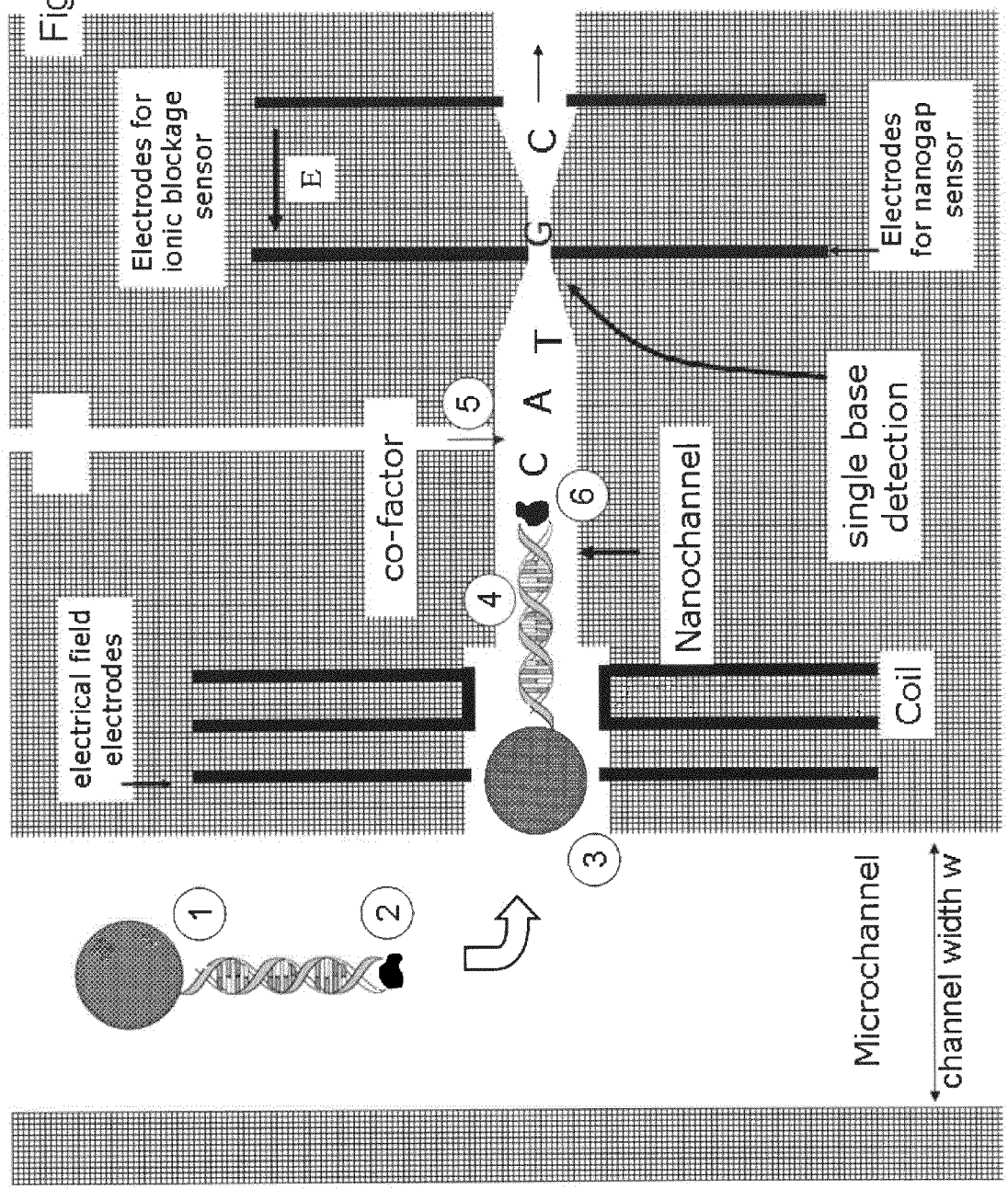

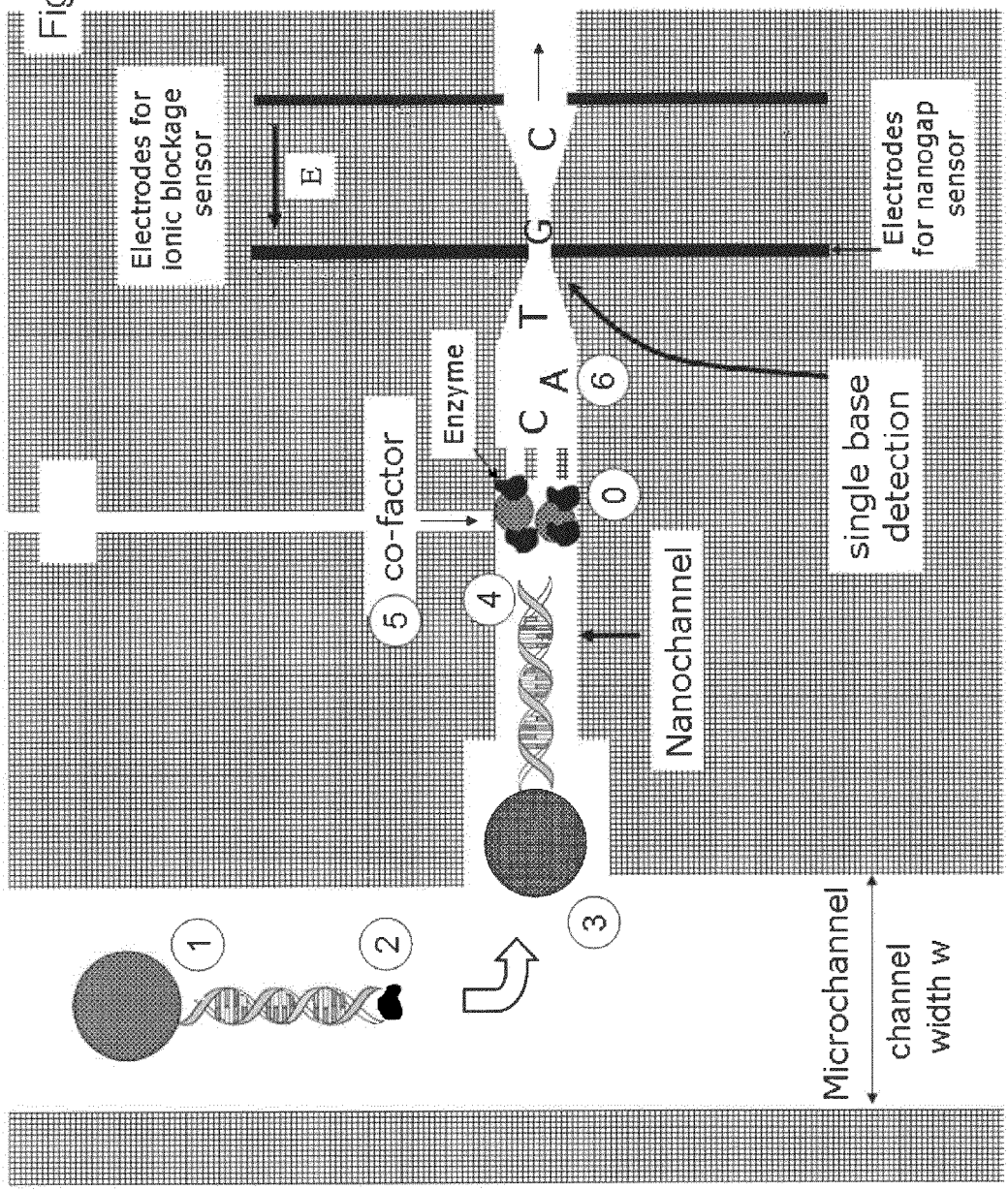

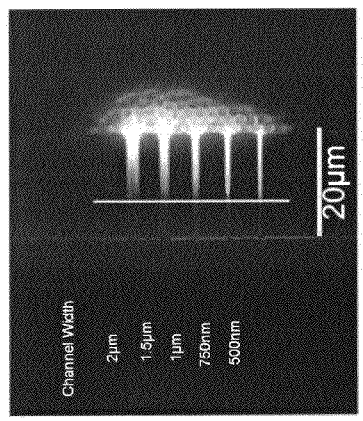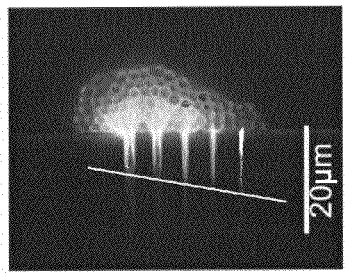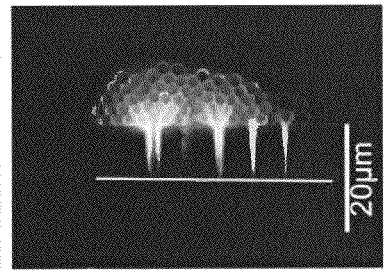
Figure 14a
Figure 14b
Figure 14c

DEVICE FOR PROCESSING AN ANALYTE AND A METHOD OF PROCESSING AND/OR DETECTING AN ANALYTE USING SAID DEVICE

The present invention relates to a device for processing an analyte and to a method of processing and/or detecting an analyte using said device.

The transfer of biology-inspired enzyme-driven processing of analytes like biomolecules into practical devices becomes a more and more important issue for applications like biosensing, point-of-care (PoC) diagnosis, and healthcare. Particular example applications are hand-held DNA sequencing which is necessary for individualised medicine, single-molecule level medical diagnostics for very early detection of diseases, and the ultra-high sensitive detection of biohazard compounds, drugs, environmental-sensitive compounds.

There are a number of challenges linked to the realisation of enzymatic processing and detection of analytes in artificial environments, like for example on inorganic surfaces inside micro-fluidic circuits.

One of the most crucial problems of enzymatic processing—like DNA digestion inside an artificial structure—is to transport to and localise the molecules at the desired locations, at which enzymatic processing followed by an analysis step should take place. Another important issue is to replace the analysed molecule with fresh molecules (repeated processing and detection). Often it is preferred to enhance the detection limit by pre-concentration of the analytes. And, in most biology-inspired applications, the processing and detection steps have to be performed in the liquid phase, making non-specific adsorption and degradation of enzymes at the surface walls a prominent problem.

Several approaches like the integration of specific, fixed anchor points inside nano- and µ-fluidic structures and the covalent or non-covalent immobilisation of DNA molecules to those defined anchor points have been studied (S. Matsuura et al., Nucleic Acid Research 29, 16 (2001) e79; S. Katsura et al., $1^{st}$ Annual International IEEE-EMBS Special Topic Conference On Microtechnologies In Medicine & Biology (2000) Lyon, France). However, it has been found that non-specific adsorption of DNA to the channel walls and the either too weak (non-covalent) or irreversible (covalent) binding of DNA to the anchor points make such approaches less attractive.

Optical laser traps can also be used in order to localise and fix bead-DNA assemblies inside micro-fluidic structures (K. Dörre et al., J Biotech. 86 (2001) 225-236; J. Stephan et al., J Biotech. 86 (2001) 255-267; U. Keyser et al., Nature Physics 2 (2006) 473-477). However, such setups require a large amount of hardware and are therefore not suitable for hand-held solutions.

The approach published by Washizu et al. describes the capture and covalent attachment of DNA molecules at Al electrodes using AC electric fields. The DNA can be stretched and sequentially processed by enzymes (T. Yamamoto et al., IEEE Trnas. on Industry Appl., 36, 4 (2000) 1010-1017). However, the major drawback of this approach is the reliability and reproducibility of DNA binding at a specific position along the electrode.

US 2003/0064400 A1 describes the positioning of DNA inside a micro-fluidic channel by utilising bead-DNA assemblies. The positioning of the beads was achieved simply through the trapping of the beads at the crossing of a microchannel with a nanochannel. However, the configuration and dimensions of the channels can easily lead to clogging by accumulation of beads.

Accordingly, it was an objective of the present invention to provide for an improved device for processing an analyte. It was also an object of the present invention to provide for a device that allows to immobilize single analyte molecules and to position them nearby a point of their detection/analysis. It was also an object of the present invention to provide for a method and device that allows to preconcentrate analytes in order to enhance the detection limit and sensitivity of a detector.

The objects of the present invention are solved by a device for processing an analyte, comprising a substrate, said substrate being a monolithic piece of material and containing a system of channels having at least a first type of channel, said first type of channel having dimensions in the range of from 1 µm to 1 mm in depth and width, at least a second type of channel, said second type of channel being in fluid connection with said first type of channel and having dimensions of from 1 nm to 2000 nm in depth and width, said first type of channel flowing into said second type of channel, a region of analyte processing or release, formed at a position where said first type of channel flows into said second type of channel, and a detector being in fluid connection with said second type of channel and being spaced apart from said region of analyte processing or release.

Preferably, said substrate is not a composite substrate.

In one embodiment the device according to the present invention further comprises carrier particles capable of binding an analyte, and a solvent within said system of channels capable of transporting said carrier particles within said first type of channel, wherein, preferably, said carrier particles have sizes in the range of from 0.1 nm to 1 mm, preferably from 100 nm to 5 µm.

In one embodiment said first type of channel has dimensions at least 5 times wider and deeper than the sizes of said carrier particles.

In one embodiment said first type of channel has dimensions of 10 µm to 20 µm in depth, and 10 µm to 200 µm in width, and said carrier particles have sizes in the range ≤2 µm.

Preferably, said region of analyte processing or release has a tapered structure wherein a cross-section of said system of channels decreases in discrete steps or continuously from said first type of channel to said second type of channel.

In one embodiment said second type of channel has dimensions in the range of from 100 nm to 800 nm in depth and width.

In another embodiment said second type of channel has dimensions in the range of from >1 µm to 2 µm.

In one embodiment said first type of channel additionally comprises structures of hindrance preventing an unhindered flow of matter, e.g. of a solvent and of carrier particles, in said first type of channel, wherein, preferably, said structures of hindrance are squares, rectangles, circles of matter placed into said first type of channel.

In one embodiment said carrier particles are spherical, cubical, parallelepiped or irregular in shape.

Preferably, said first type of channel has a length in the range of from 1 mm to 10 cm, and said second type of channel has a length in the range of from 1 nm to 1 mm, preferably 100 nm to 100 µm.

In one embodiment said detector is at a distance from said region of analyte processing, said distance being in the range of from 1 nm to 1000 μm, preferably 5 nm to 1 μm.

In one embodiment said detector is selected form the group comprising biological pore proteins, artificial nanopores, nanogap sensors, electrochemical sensors, optical-spectroscopical sensors, mass-spectroscopical sensors, Raman-spectroscopical sensors, FTIR spectroscopical sensors.

In one embodiment the device according to the present invention further comprises means to introduce and/or maintain a flow of solvent and carrier particles through said system of channels, wherein, preferably, said means to introduce and/or maintain a flow exert electric, magnetic, electromagnetic or hydrodynamic forces on said solvent and/or said carrier particles.

In one embodiment the device according to the present invention further comprises means to immobilize said carrier particles at said region of analyte processing or release, wherein, preferably, said means to immobilize exert electric, magnetic, electromagnetic or hydrodynamic forces on said solvent and/or said carrier particles.

In one embodiment said substrate is made of a material selected from silicon, silicon oxide, glass, polymers e.g. PDMS, polycarbonate, PE, silicone, and said system of channels is formed by ebeam-writing, etching, molding, focused ion-beam etching, laser ablation, embossing, wherein, preferably, said substrate is made of a polymer or a combination of polymers, and said substrate is formed as a monolithic piece of material by molding or embossing said polymer using a master in which a negative image of said system of channels has been provided.

In one embodiment said carrier particles are made of a material selected from silicon oxide, $Al_2O_3$, metallic and/or magnetic materials, such as Au, Ag, Pd, Pt, Al, Ti, Fe, Ni, ceramics, and polymers, such as polymethylmethacrylate (PMMA), polystyrene, teflon, melamine, polylactide, dextran.

In one embodiment said carrier particles further comprise analyte-binding groups which interact with a corresponding carrier particle-binding group on said analyte, wherein, preferably, a pair of analyte-binding group and corresponding carrier particle-binding group is selected from the group comprising biotin/(strept)avidin, antibody/antigen, gold/thiol modifications, Nickel/$His_6$, lectine/sugar, glutathione/glutathione-S-transferase, $NH_2$/COOH/epoxy covalent binding, Protein A, G binding with high affinity to the $F_c$ portion of various classes and subclasses of immunoglobulins from a variety of species, hydrogen bonds or is based on DNA-base hybridisation, aptamer binding, e.g. protein-DNA/RNA interaction, collagen/collagen-binding proteins, Dig/anti-digoxigenin, or is based on hormone binding, or is based on other electrostatic, ionic, and/or covalent interactions.

In one embodiment said system of channels is modified at the surface of said channels by application of a chemical species to reduce a non-specific adsorption of analytes on the surface, wherein, preferably, said modification is performed through liquid phase deposition or gas phase deposition, preferably gas phase deposition, more preferably gas phase deposition of a silane.

In one embodiment said surface of said channels is selected from polymer e.g. PDMS, and silicon oxide, wherein, preferably, said modification is performed by exposing said surface to silane compounds having chemical endgroups, such as methyl-, amino-, fluoro- or thiol-groups, or other molecular species that expose hydrophobic groups to the channel surface.

In one embodiment the device according to the present invention further comprises means to release said analyte from said carrier particle at said region of analyte processing or release, wherein, preferably, said means to release said analyte perform such release based on photoinduced release, electric field-induced release, temperature-induced release, chemical reaction, or biochemical reactions e.g. with co-factors, enzyme mediated-induced release of said analyte from said carrier particle.

In one embodiment the device according to the present invention further comprises means to further process said analyte by chemical reaction, e.g. cleavage into smaller fragments or building blocks, wherein, preferably, said means to further process said analyte by chemical reactions are carrier beads on which a chemical agent, preferably an enzyme, is immobilized.

In one embodiment said analyte is selected from nucleic acids, such as single strand, double strand DNA, RNA, proteins, polypeptides, drugs and other molecules which are in liquid phase or gas phase under ambient conditions, biologically or environmentally hazardous molecules.

The objects of the present invention are also solved by a method of processing and/or detecting an analyte, comprising the steps:
  binding an analyte to a carrier particle as defined above
  transporting said carrier particle and analyte bound thereto through said system of channels of a device according to the present invention to said region of analyte processing or release in said device
  immobilizing said carrier particle and analyte bound thereto at said region of analyte processing or release
  releasing said analyte from said carrier particle by applying light, electrical field, magnetic field, electromagnetic field, heat or cold, or by performing a chemical or biochemical cleavage reaction e.g. using enzymes like nucleases, proteases, e.g. Exo I, Exo III, Sfo I, Xba I and other restriction enzymes,
and/or processing said analyte by performing a chemical or biochemical cleavage reaction e.g. using enzymes like nucleases, proteases, e.g. Exo I, Exo III, Sfo I, Xba I and other restriction enzymes,
  transporting said released analyte or said processed analyte or said released and processed analyte to said detector
  detecting said released analyte or said processed analyte or said released and processed analyte using the detector as defined above.

In one embodiment the method according to the present invention further comprises the step of removing said carrier particle from said region of analyte processing or release, after said analyte has been released and/or processed.

Preferably, said transporting steps and said removing step are performed using said means to introduce and/or maintain a flow of solvent and carrier particles as defined above.

In one embodiment said immobilization step is achieved by the dimensions of said region of analyte processing or release or by said means to immobilize said carrier particles as defined above, or by a combination of both.

Preferably, said detecting step using said detector occurs by optical detection, chemical detection, electrical detection, magnetic detection, electrochemical detection.

In one embodiment said analyte is nucleic acid, said step of processing said analyte is enzymatic degradation of said nucleic acid, and said step of detecting said processed analyte includes detection of single nucleotides or nucleotide bases to elucidate the sequence of said nucleic acid.

In one embodiment said enzymatic degradation is performed by adding carrier beads into said system of channels, on which carrier beads enzymes for said enzymatic degradation have been immobilized.

The objects of the present invention are also solved by a method of producing a device according to the present invention comprising the following steps:
  providing a master having a negative image of said system of channels as defined above
  molding or embossing said substrate using said master and a polymeric material or a material suitable to form a polymer, thereby obtaining said substrate as a monolithic piece of polymeric material, said substrate containing said system of channels.
Preferably, the method further comprises the step:
  covering said system of channels with a plate, such as a glass plate.

In one embodiment said negative image of said system of channels of said master is formed by a process selected from ebeam-writing, etching, ion beam etching, laser ablation, photolithographic techniques and combinations thereof.

The term "monolithic piece of material", as used herein in connection with the substrate is meant to refer to a scenario wherein the substrate is made as a unitary piece of material. For example US 2003/0064400 describes the manufacture of a device having a system of differently sized channels in it, wherein each type of channel is confined to a different substrate, and these substrates are subsequently combined, for example glued together. Such an assembled substrate is herein also referred to as a "composite substrate", and the substrate according to the present invention is not such a "composite substrate". Rather, the term "monolithic", as used herein, is meant to refer to a scenario wherein there is a single substrate made from one piece of material which does not involve the assembly of different parts or components together for example through gluing or other means of mechanical connection. Rather, in the substrate according to the present invention, there is a single piece of material in which the system of channels is present. This is also herein sometimes referred to as the system of channels "being embedded in said substrate". In contrast to the "single substrate" or "unitary substrate" or "non-composite substrate" in accordance with the present invention, there is more than one substrate or a "composite substrate" in US 2003/0064400. In preferred embodiments according to the present invention, the substrate according to the present invention is formed from a monolithic piece of material or single piece of material which, in preferred embodiments is made of a polymer or a combination of polymers and is formed by molding such polymeric material using an appropriate master wherein a negative image of the system of channels has been previously formed. In another embodiment, such appropriate master may be used for embossing, e.g. hot embossing, into the polymeric material. The person skilled in the art knows how to form an appropriate master, for example starting from a silicon wafer or $SiO_2$-wafer and using an appropriate sequence of deposition and removal steps, such as ebeam-writing, etching, focused ion-beam etching, laser ablation, and other photolithographic techniques, in order to create said system of channels. Examples of how to form such suitable master are given later in the current application.

The term "a system of channels", as used herein is meant to refer to a network of channels which are fluidly interconnected. The term "in fluid connection with" is meant to characterize the spatial relationship between two channels which relationship requires that matter, such as a liquid may be transported or flow from one channel into the other channel.

"A first type of channel" is meant to refer to a specific type of channel characterised by having dimensions in the range of from 1 μm to 1 mm in depth and width. The length of such channel may vary. Such "first type of channel" is herein also referred to as "a micro channel".

"A second type of channel" is meant to refer to another type of channel characterised by having smaller dimensions, namely in the range of from 1 nm to 2000 nm in depth and width. Again, the length of such channel may vary. This "second type of channel" is also herein sometimes referred to as a "nano channel". The "first type" and "second type" of channel are in fluid connection with each other.

The term "said second type of channel is embedded in said first type of channel", as used herein is meant to refer to a spatial arrangement, wherein the second type of channel is fully engulfed by said first type of channel "A region of analyte processing or release", as used herein, is meant to refer to the region in which the first type of channel forms the fluid connection to the second type of channel, such that the cross-sectional area of a flow path through this system of channels is reduced from the dimensions of the first type of channel to the dimensions of the second type of channel. This "region of analyte processing or release" is herein also sometimes referred to as a "micro-to-nano-transition" or "-constriction". In this "region of analyte processing or release", usually carrier particles having an analyte bound thereto are immobilized such that the analyte may be released and/or further processed. Usually such further processing then takes place whilst the analyte is still bound to the carrier particle or whilst the analyte is in said second type of channel (nano channel). Preferably, this region of analyte processing or release has a "tapered structure", and the decrease of cross-sectional area of a flow path is either in discrete steps or is continuous. In preferred embodiments, the first type of channel has dimensions which are at least five times wider and deeper than the sizes of said carrier particles. This has proved to give particularly good results when clogging and accumulation of carrier particles is to be avoided. Likewise, the second type of channel has dimensions of the same size or smaller than the carrier particles in order to prevent the carrier particles from entering the second type of channel. However, the analyte that is bound to the carrier particle may proceed into said second type of channel, and further steps, such as chemical processing, may ensue.

The term "tapered structure", as used herein, in connection with the system of channels is meant to refer to a scenario, wherein the channel width/diameter/cross section decreases from the first type of channel to the second type of channel. Such decrease may be gradual or may occur in discrete steps. Such tapered structure may be provided for by creating an appropriate negative image of such tapering in the master using the aforementioned etching and deposition techniques and other photolithographic techniques.

It is also clear to someone skilled in the art that the flow pattern within said first type of channel may be influenced by the introduction of "structures of hindrance", such as intermittent (partial) walls, squares, rectangles, circles of matter that are placed into the flow path of said first type of channel.

In preferred embodiments, the surface of the system of channels, preferably of the first type of channels or of the second type of channels or of both, may be surface modified by exposing the surface of the channels to a gaseous phase of a silane compound. The inventors have found that this reduces non-specific adsorption of analytes on the surface. By such action, the surface of the channels may be made moderately hydrophobic, having contact angles in water around 60°. The preferred gas phase deposition, e.g. silanisation in the gas phase, ensures that also the surface of the second type of channels (nanochannels) gets modified. In particularly preferred embodiments, the silane compound has methyl-groups which greatly reduce the non specific adsorption of analytes, such as nucleic acids, on the surface, whilst avoiding the (undesired) immobilization of double-stranded nucleic acids.

Liquid phase deposition, whilst also being possible to modify the surface of the channels, is less preferred, as it often does not access features of the channel system on the nanoscale, and additionally, it frequently relies on the presence of organic solvents (forming the liquid phase), which solvents are not compatible with a number of polymers that one would like to use for the substrate according to the present invention, such as polydimethyl siloxane (PDMS).

Using the device according to the present invention allows to pre-concentrate analytes for subsequent detection through a detector in accordance with the present invention. Thereby, the sensitivity of the detector may be improved, and the detection limit performance of the detector is enhanced.

Detection of said analyte may occur by a number of means, most notably biological pore proteins, artificial nanopores, nanogap sensors, electrochemical sensors.

The readout of these sensors is preferably done electrically. In the case of biological pore proteins or artificial nanopores, a voltage is applied across the pore as schematically shown in FIG. 5a. The applied potential drives an ionic current through the pore and as soon as an object like a DNA base translocates through the pore, the ionic current is reduced for a short moments (e.g. Akeson et al. Methods and devices for characterizing duplex nucleic acid molecules, U.S. Pat. No. 6,936,433 B2, 2005; experimentally shown for DNA bases by Y. Astier, O. Braha, and H. Bayley, *Toward Single Molecule DNA Sequencing: Direct Identification of Ribonucleoside and Deoxyribonucleoside 5'-Monophosphates by Using an Engineered Protein Nanopore Equipped with a Molecular Adapter*, J. Am. Chem. Soc., 128(5), pp. 1705-1710, (2006)).

In the case of nanogap sensors, the molecules travel through a 1-3 nm wide electrode gap. The published concept predicts that the tunnel current which flows across the 1-3 nm could be modulated by the individual dielectric properties of the translocating molecule (theoretically predicted by J. Lagerqvist, M. Zwolak, M. Di Ventra, "Fast DNA Sequencing via Transverse Electronic Transport", Nano Lett. 6 (4) (2006) 779-782; M. Zwolak, M. Di Ventra, "Electronic Signature of DNA Nucleotides via Transverse Transport", Nano Lett. 5 (3) (2005) 421-424).

The solvent that may be used to achieve transport of carrier particles in said system of channels may be water, aqueous solutions, organic solvents, such as ethanol, propanol and mixtures thereof, mixtures of organic solvents with water etc.

The device according to the present invention also comprises "means to introduce or maintain a flow" of solvent through said systems of channels, and "means to immobilize said carrier particles at said region of analyte processing or release". Both these means usually make use of the application of an electric or magnetic field or electromagnetic field or simply the exertion of hydrodynamic forces. In the simplest case, such means may be a pump or a syringe by the action of which solvent is pressed through the channels. Alternatively, such means may be a magnet or a set of electrodes positioned at suitable places at, around or in said system of channels or said region of analyte processing or release.

The term "to exert electric, magnetic or electromagnetic forces", as used herein, is meant to refer to the application of an electric, magnetic or electromagnetic field. Hydrodynamic forces may be applied by application of a pressure potential.

The attachment of an analyte to a carrier particle occurs via a linkage achieved between an analyte-binding group on said carrier particle and a corresponding carrier particle-binding group on said analyte.

The number of analytes per carrier particle can vary between 0 and x, where, in preferred embodiments, x=>1 and x is influenced by the analyte concentration and the maximum possible packing density of the specific analyte on the carrier surface. The number of analytes is automatically adjusted by the presented analyte concentration. For nucleic acid sequencing, e.g. DNA sequencing, 1 analyte per carrier would be preferable, which can be achieved by careful nucleic acid concentration adjustment during the nucleic acid-carrier assembly step. In other embodiments, however, x may be >1, e.g. gas phase detection applications.

The release of the analyte from said carrier particle may be achieved by photoinduction, induction through application of an electric field, temperature induction or induction through a chemical reaction. Likewise, the further processing may be achieved through a chemical reaction. For example the analyte may be cleaved into smaller fragments by addition of appropriate chemical agents or enzymatic degradation. More specifically, in the case of enzymatic degradation, such degradation may be triggered by the addition of appropriate co-factors without which the enzyme may not be functioning yet.

In a preferred embodiment, the entire set-up may be used for example for sequencing purposes of nucleic acids, e.g. DNA, whereby single nucleotides/single nucleotide bases are detected in the order in which they occur within the analyte nucleic acid.

In one embodiment of this sequencing device, a bead-nucleic acid assembly, i.e. nucleic acids immobilized on beads, is trapped in a micro- to nano-transition, and the immobilization occurs by the mere dimensions of this transition and/or through the application of an electrical or magnetic or electromagnetic field. The electrical field may be applied using electrodes. An enzymatic digestion of the nucleic acid is started by adding an appropriate co-factor for the exonuclease enzyme which is also added to the reaction mixture. The released bases are detected at the end of the nano-channel using a molecular detector. In an alternative embodiment, exonuclease enzymes could be linked to separate beads which may get trapped inside the second type of channels using hydrodynamic forces (micro-to-nano-transition), electrical, magnetic or electromagnetic fields. The nucleic acid is bonded to further beads and is trapped using also hydrodynamic forces or electrical, magnetic or electromagnetic fields. The beads carrying the enzymes and the beads carrying the nucleic acid may have different sizes. The advantage of this alternative embodiment is that the distance between the enzymes and the detector stays constant, because the beads are immobilized at a certain position within the flow path. The distance between the nucleic acid carrier bead and the enzyme may need to be controlled by an external field, such as magnetic, electric or electromagnetic field, or by means of flow. This alternative embodiment is shown in FIG. 5c.

Reference is now made to the figures, wherein

FIG. 5a and FIG. 5b shows a device concept for sequencing DNA by utilizing a bead-DNA assembly, which is trapped in a micro-to-nano constriction (with or without electrical field electrodes. Enzymatic digestion of the DNA is started by adding the co-factor and the released bases are detected by using a molecular detector. FIG. 5c shows the alternative idea of having the enzyme(s) immobilized on the surfaces of carrier beads.

Figure 1:
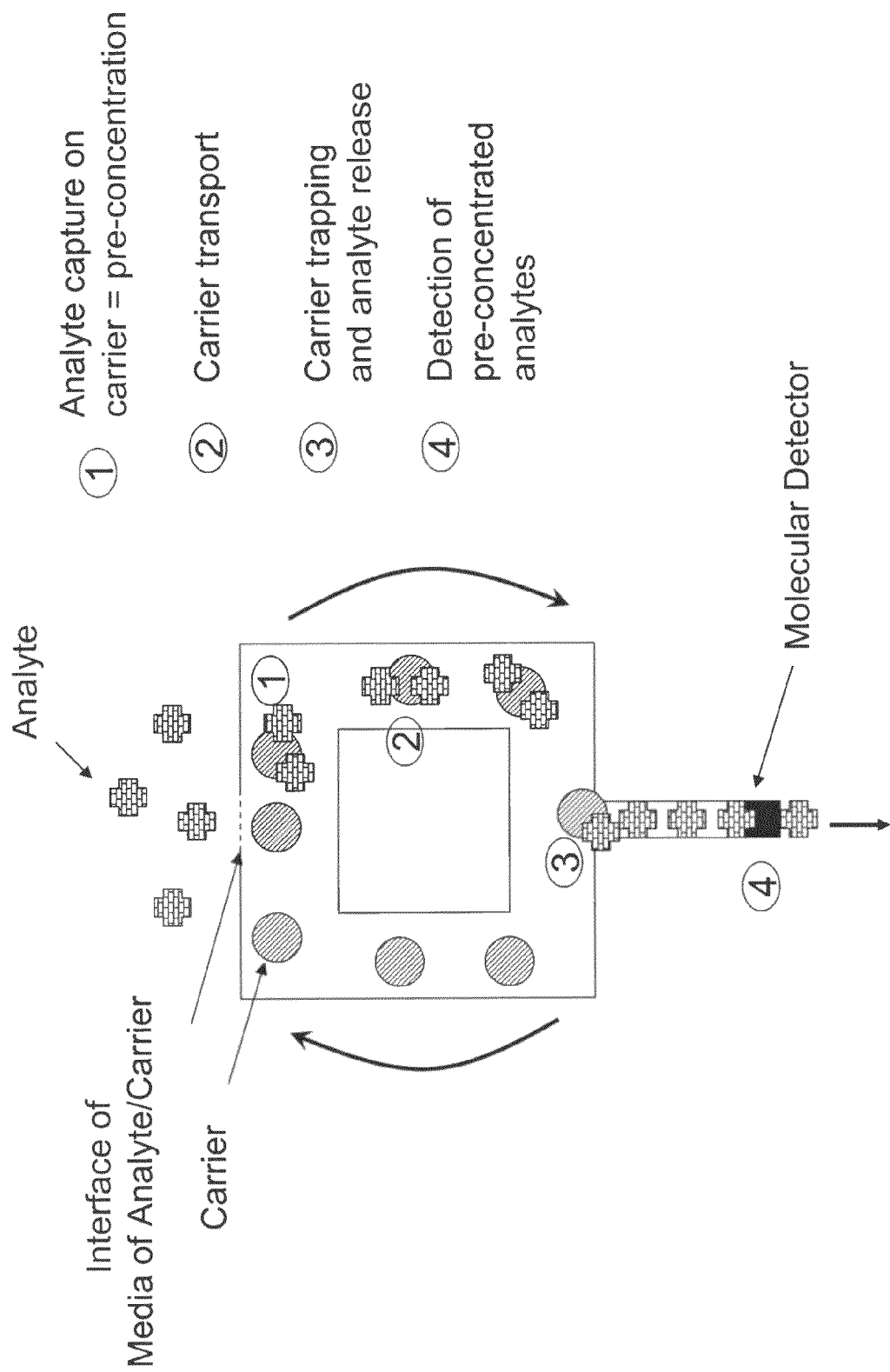
FIG. 1 shows a schematic description of the approach of using a carrier to capture, transport and release analytes in the vicinity of a molecular detector.
Figure 2:
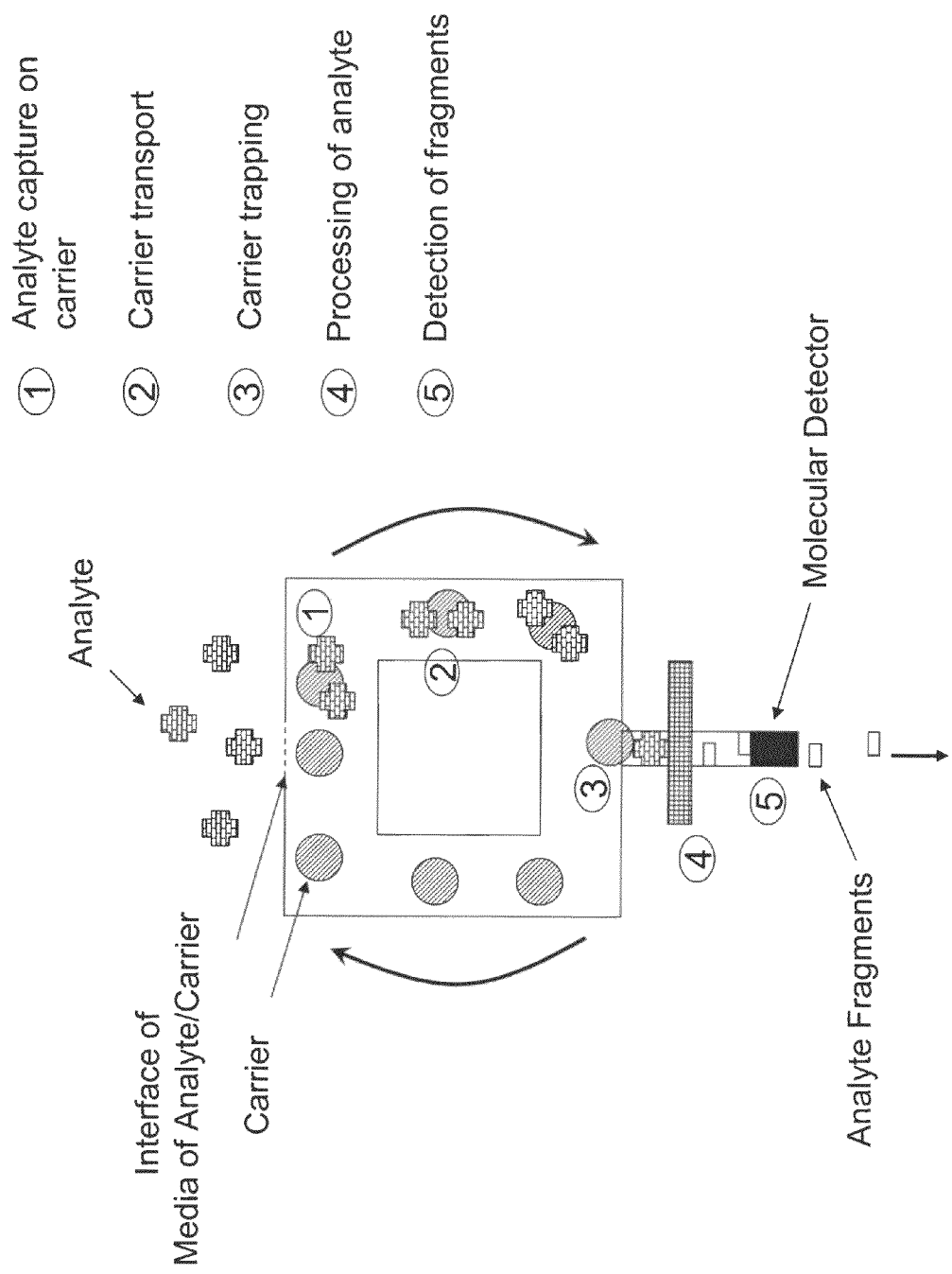
FIG. 2 shows a schematic description of the approach of using a carrier to capture, transport and release analytes in the vicinity of a molecular detector. In this case, the analytes are processed prior to their detection.
Figure 3:
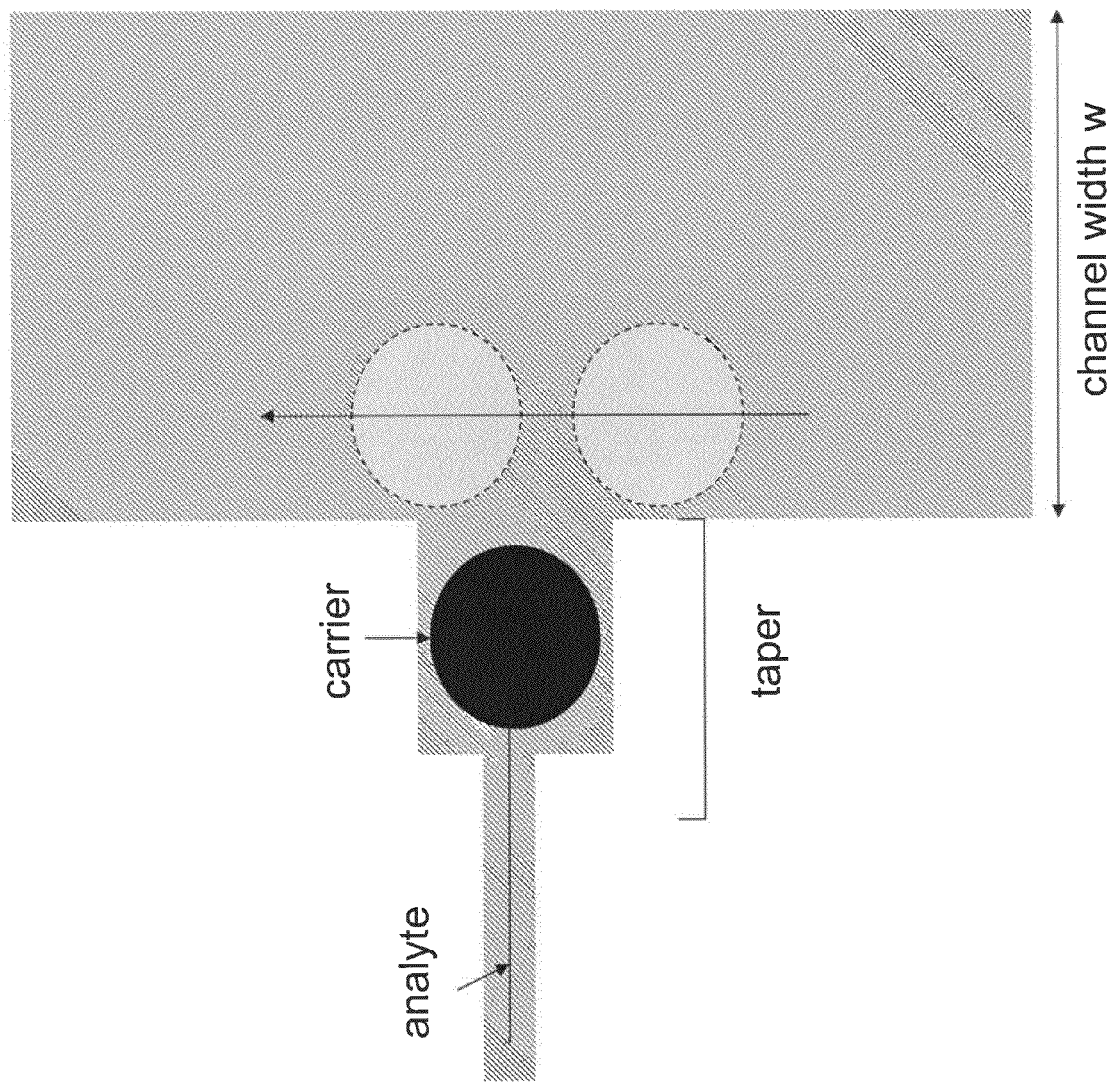
FIG. 3 shows a tapered micro-to-nano transition to enable the trapping of single carriers.
Figure 4:
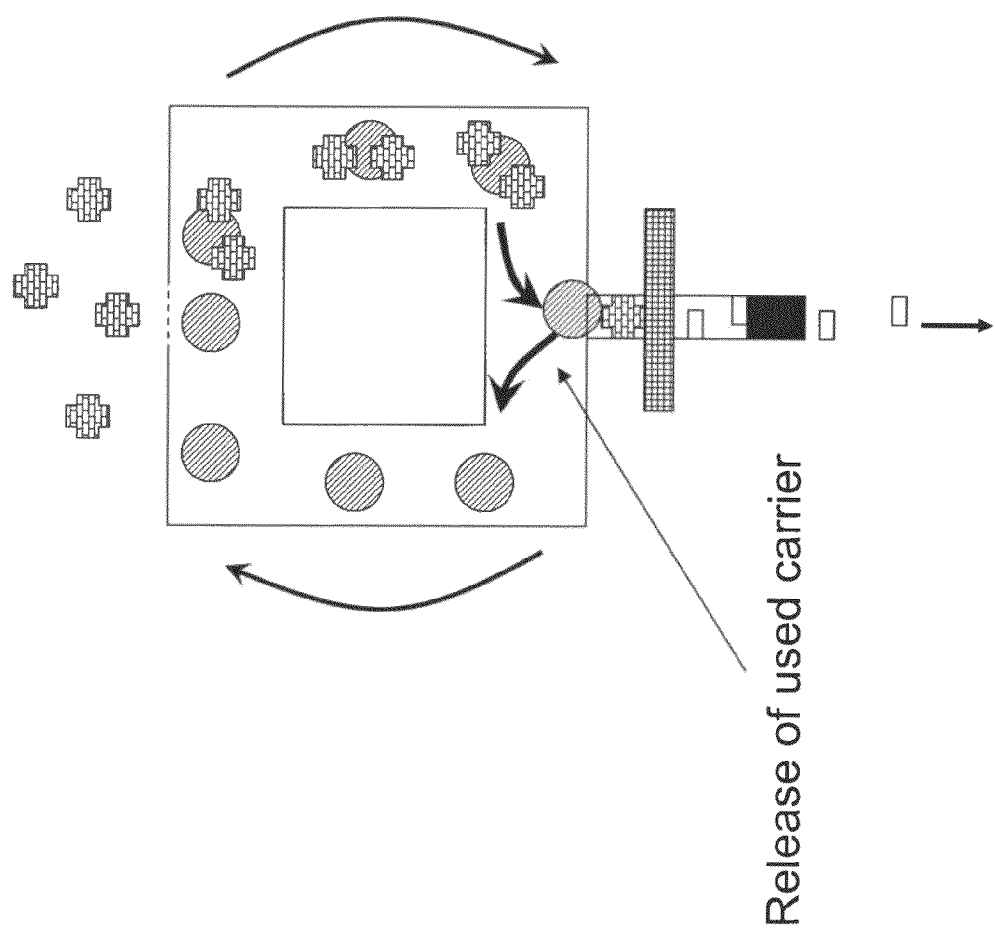
FIG. 4 shows a schematic view on the replacement of a carrier.
Figure 6:
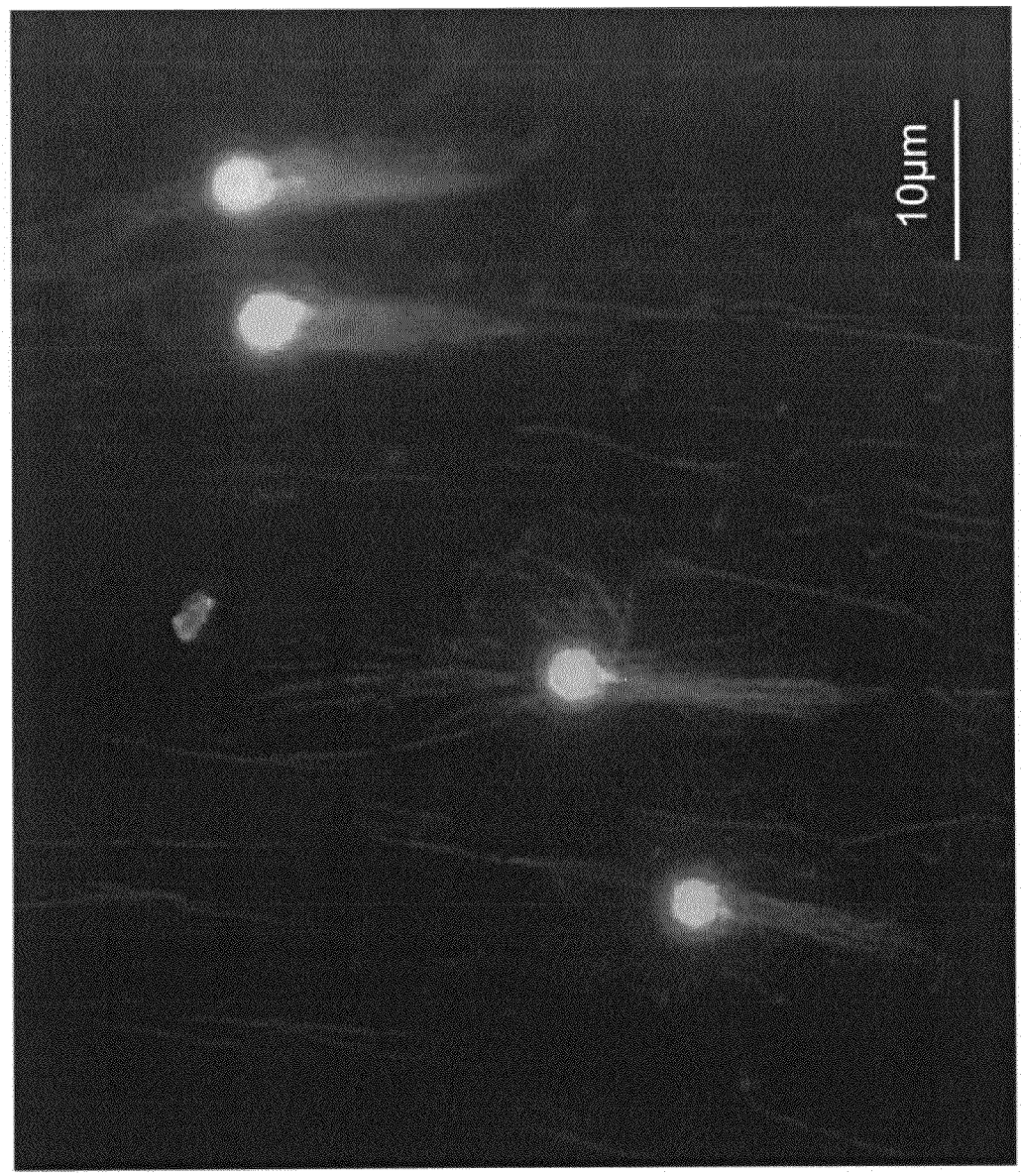

FIG. 6 shows a fluorescence image of a DNA-bead assembly in solution on a glass surface.

Figure 7A:
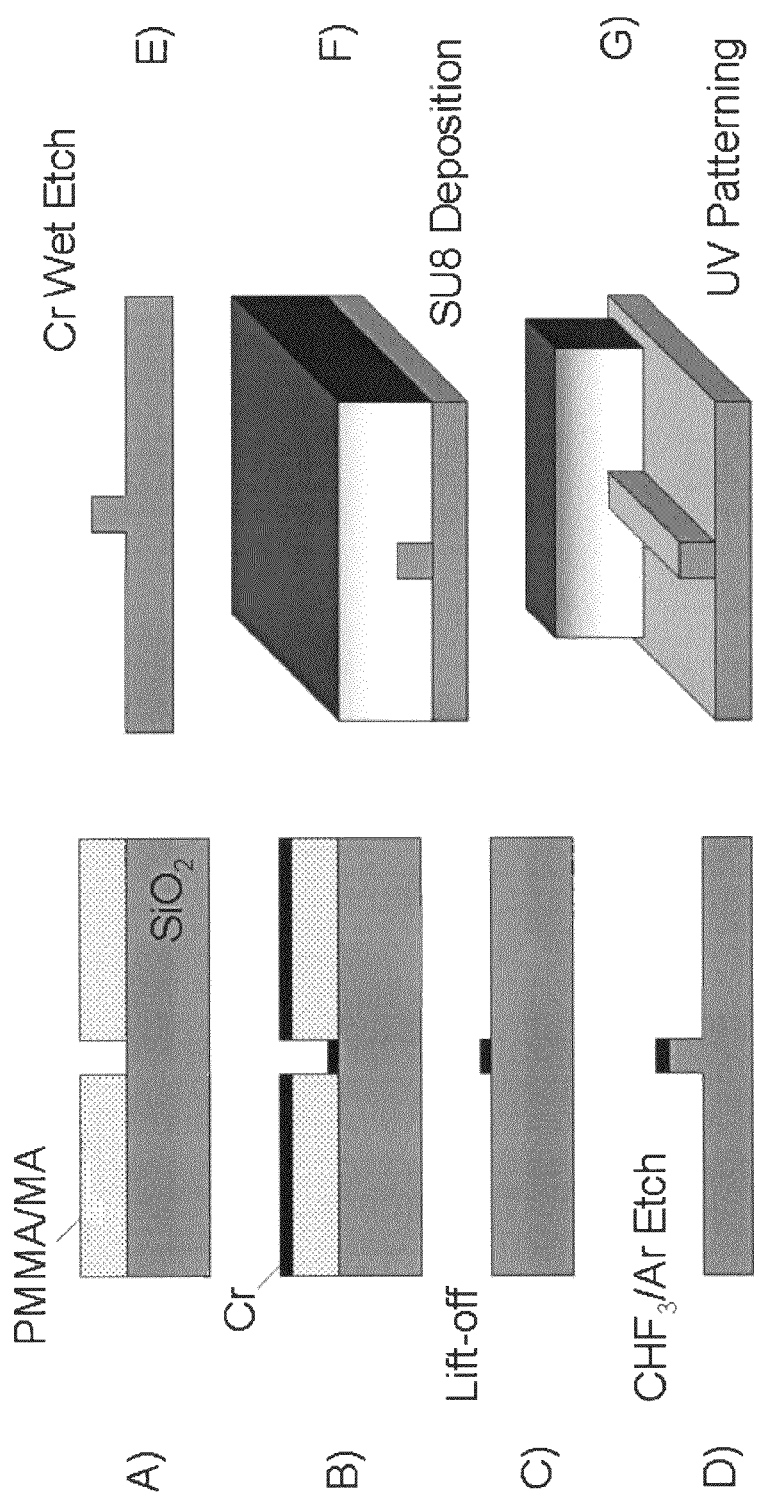
Figure 7B:
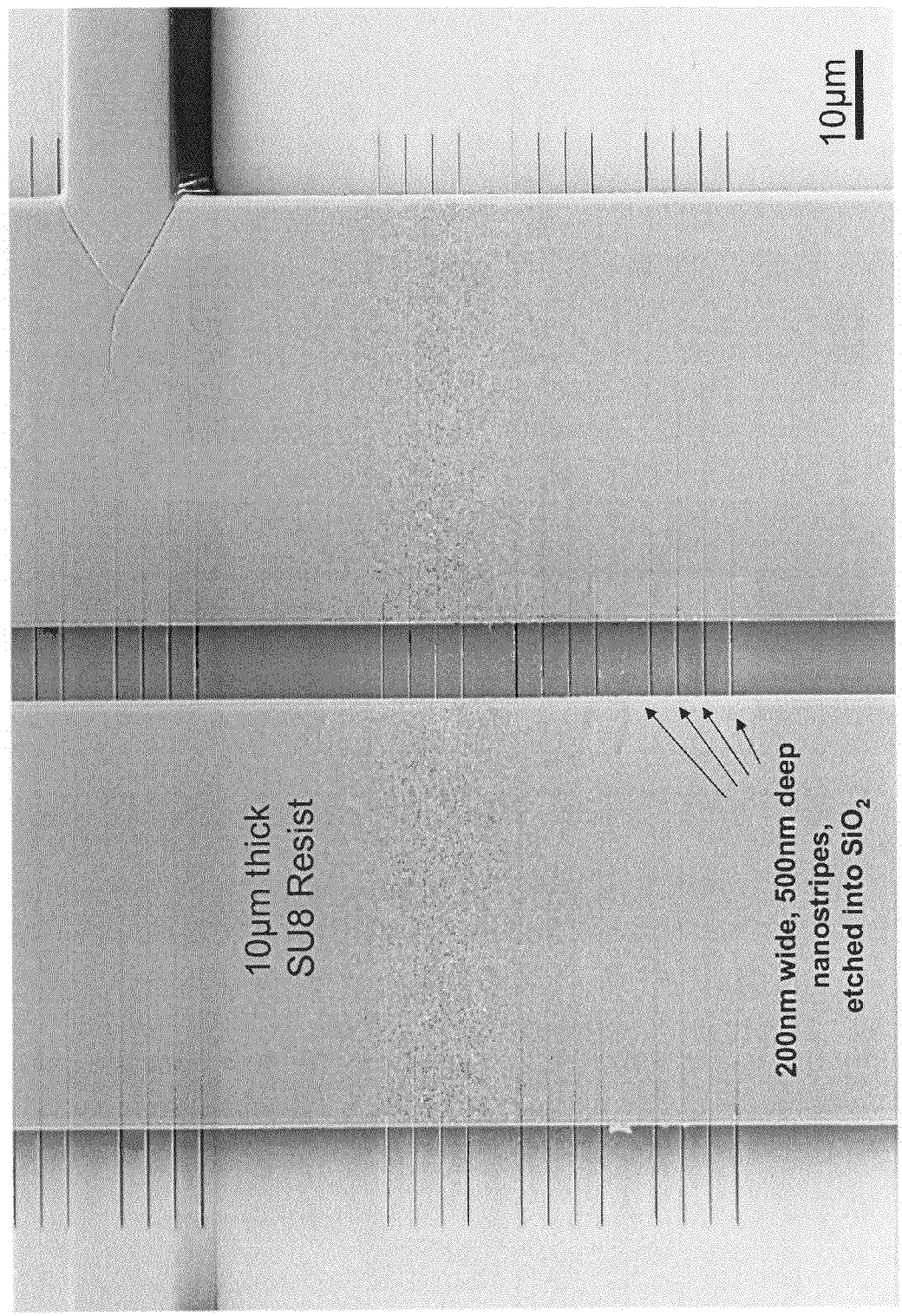

FIG. 7a shows the process-steps of the master fabrication and FIG. 7b shows the SEM image of a fabricated master structure on a silicon wafer that can subsequently be used for PDMS molding to realise the micro-to-nano transition.

FIG. 8 shows fluorescence images of reduction of non-specific adsorption of 16 µm long λ-DNA molecules on micro-fluidic channel surfaces that are covered with methyl-triethoxysilane through gas-phase silanisation. (a) non-silanised (b) silanised.

Figure 9:
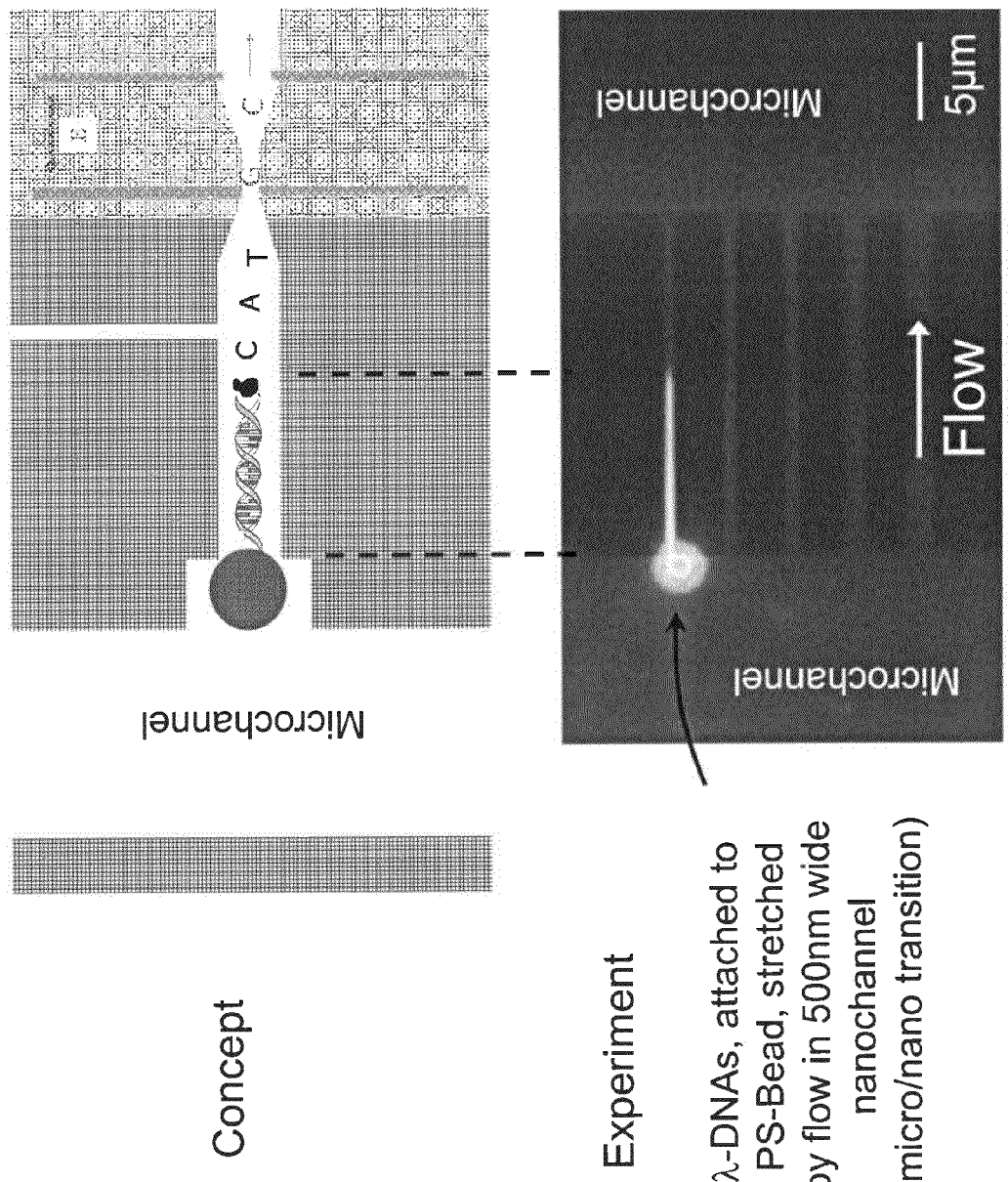

FIG. 9 shows the micro-to-nano-transition and the trapping of one DNA-bead assembly in a 500 nm wide channel. The DNA molecules get stretched into the nanofluidic channel by hydrodynamic forces.

Figure 10:
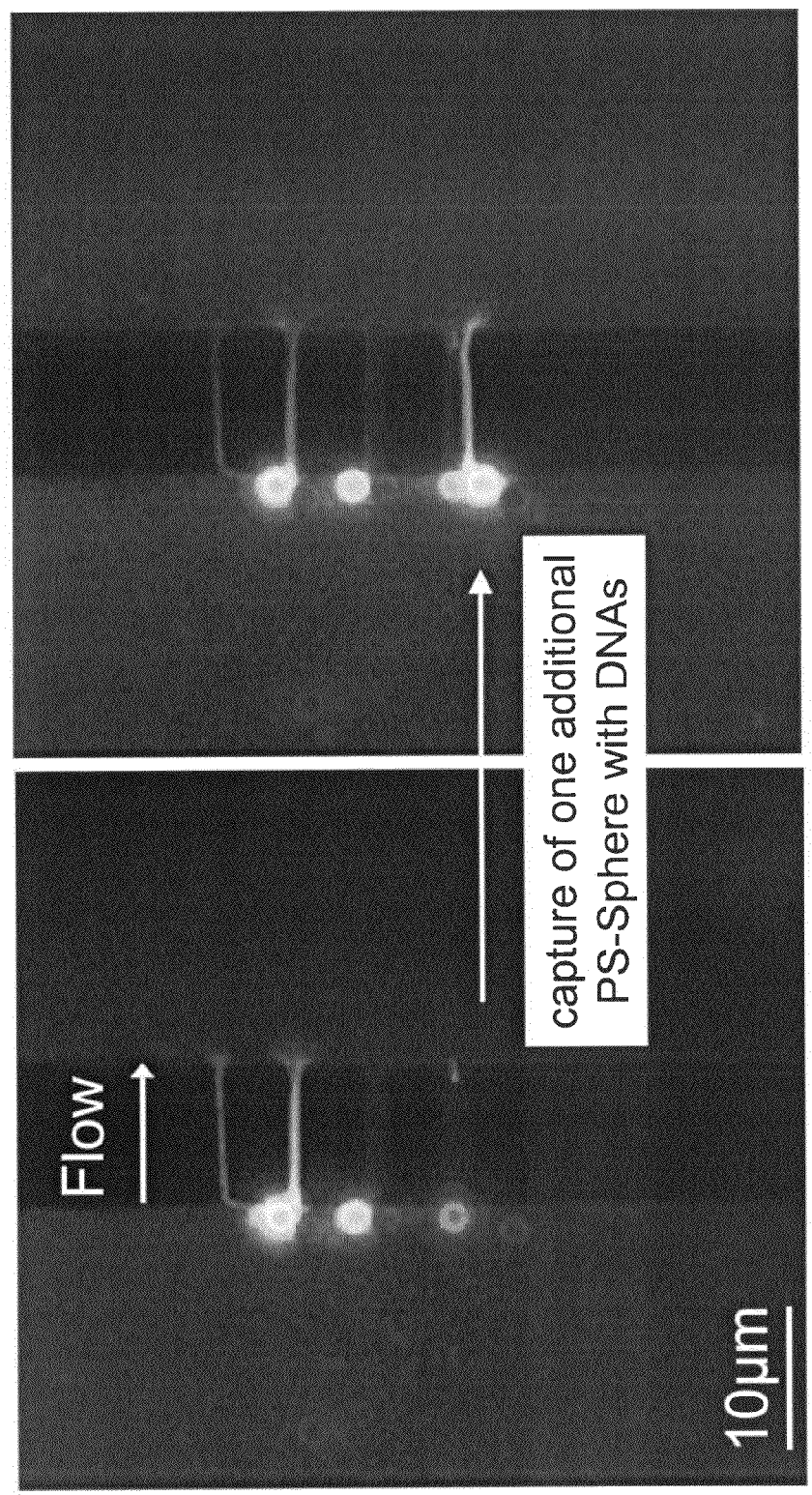

FIG. 10 shows fluorescence images of the addition of one DNA-bead assembly to already trapped assemblies.

Figure 11A:
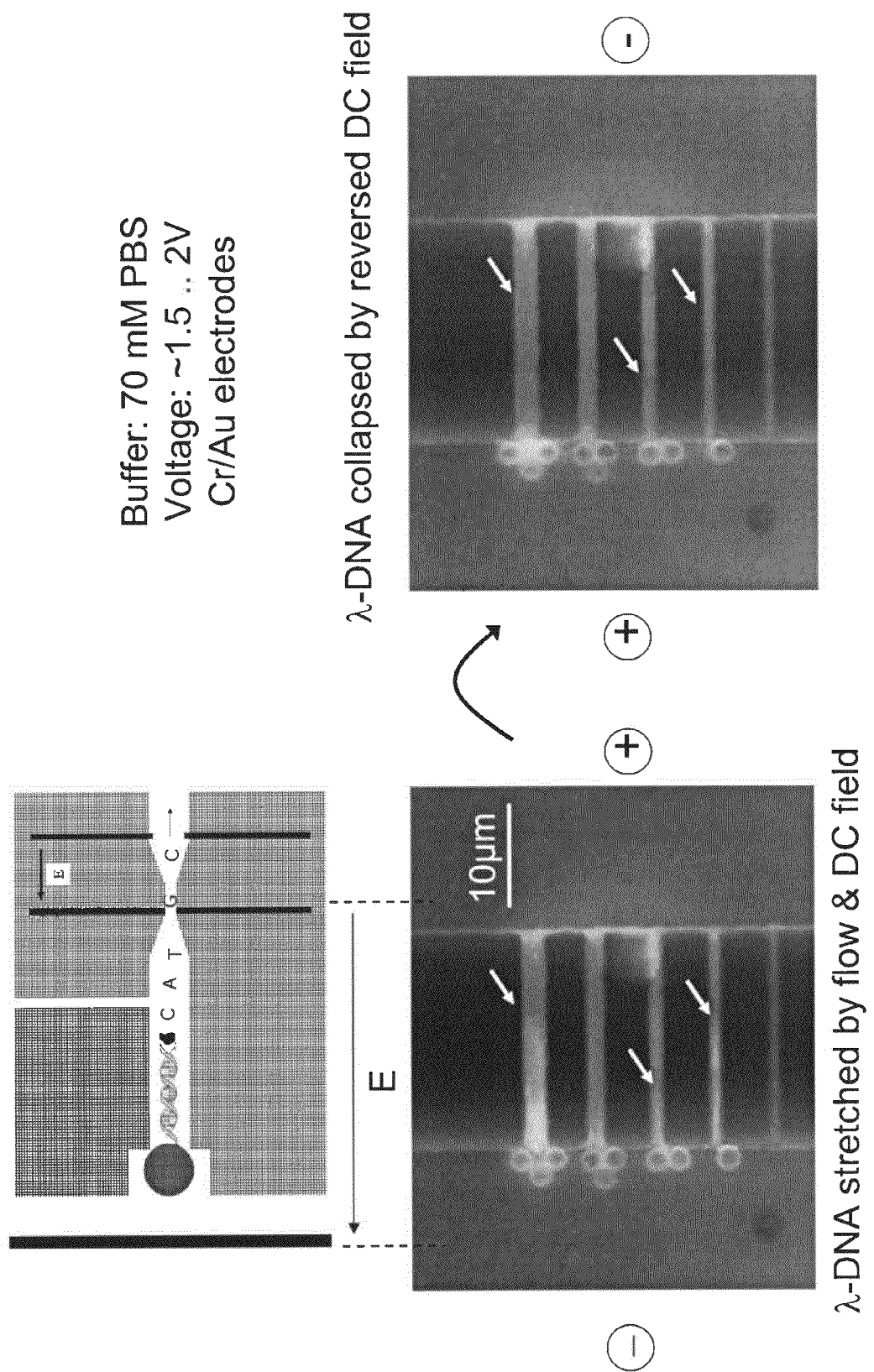
Figure 11B:
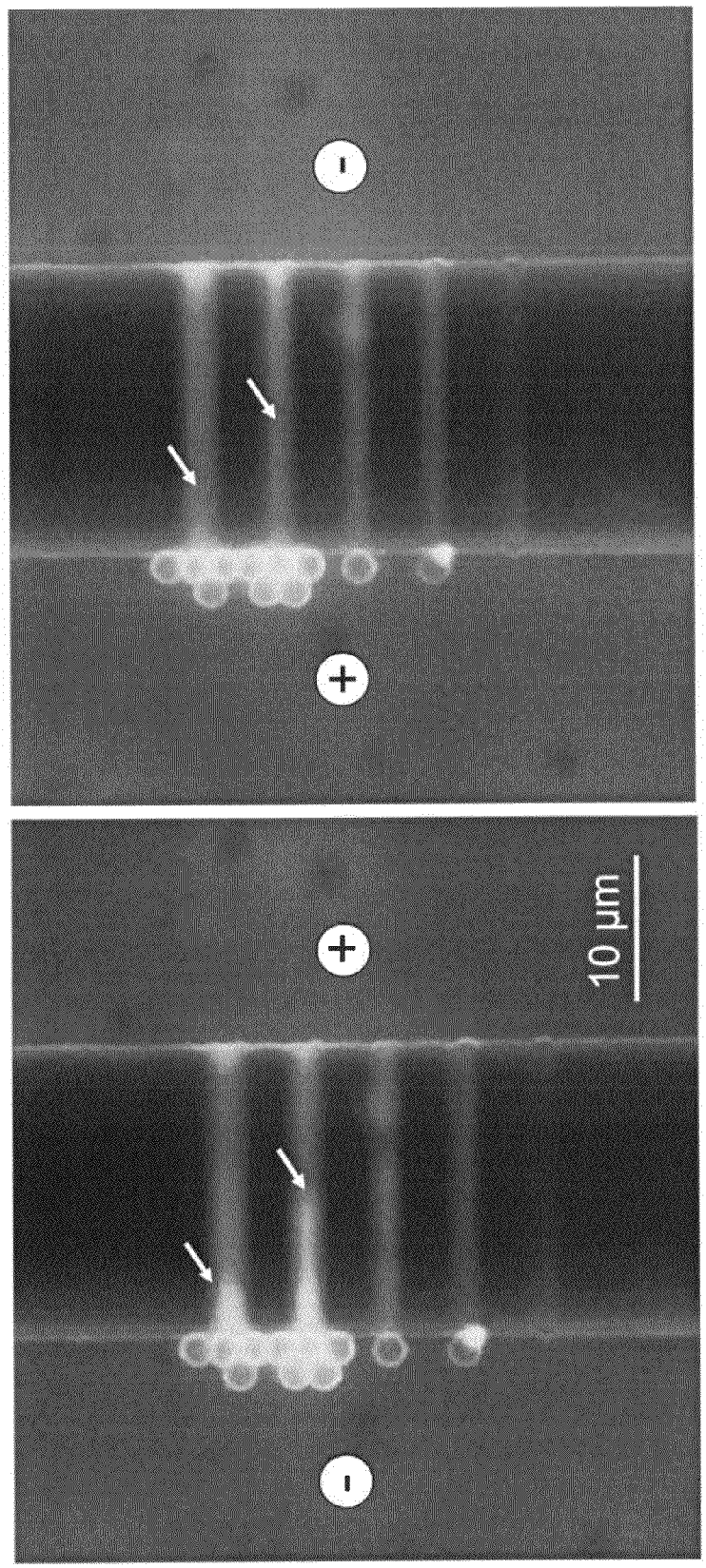
Figure 11C:
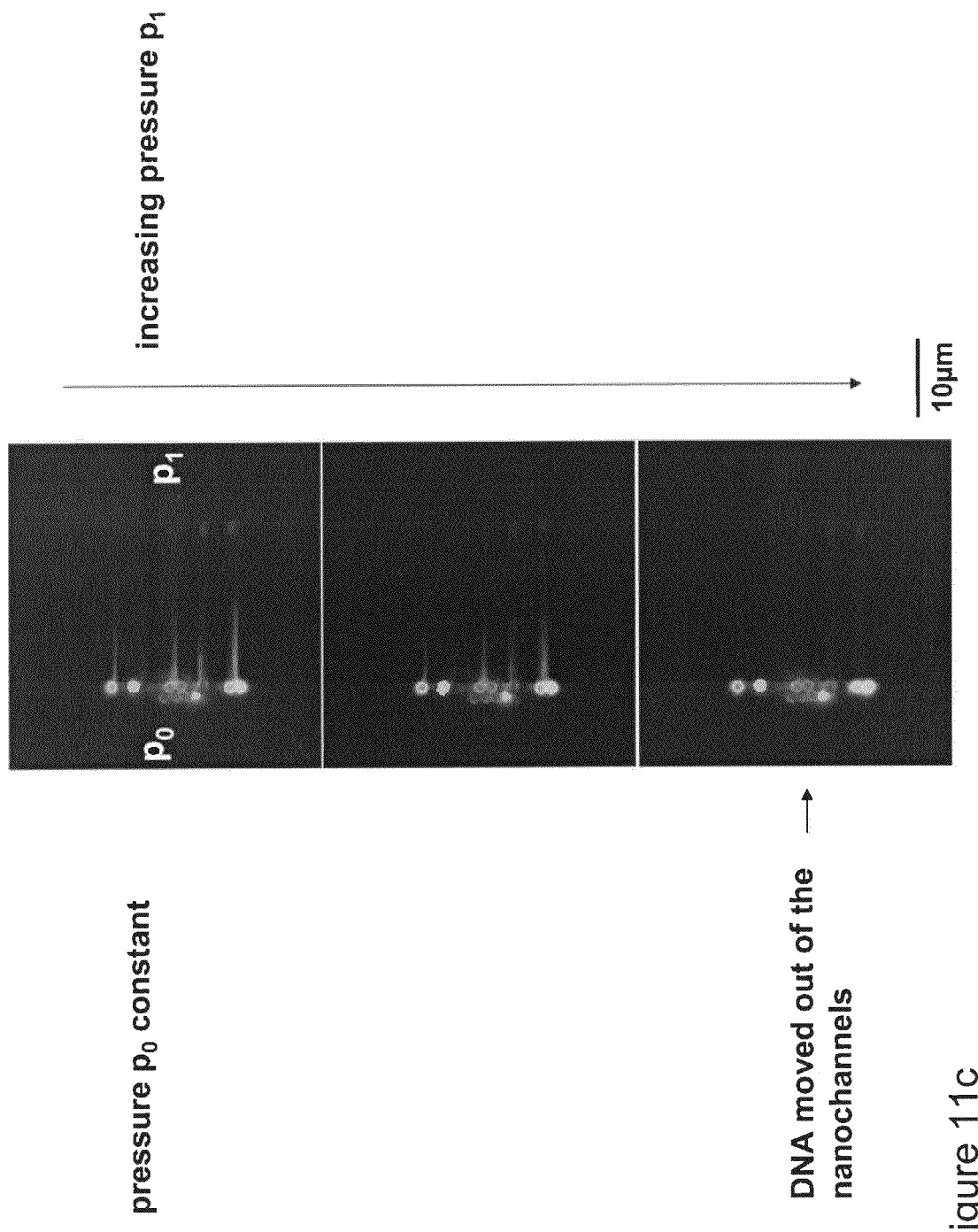
Figure 12:
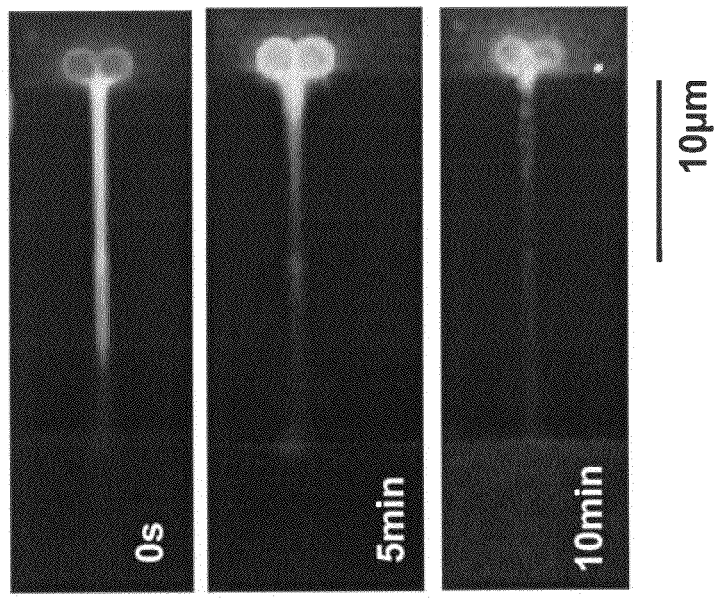

FIG. 11a and FIG. 11b show fluorescence images of the manipulation of the trapped DNA by using electric DC fields. FIG. 11c shows the manipulation by reversed hydrodynamic flow. A 10 µm bar scale is shown FIG. 12 shows fluorescence images of the digestion of trapped DNA using an exonuclease enzyme, at t=0 s (upper panel), t1=5 min (middle panel), t2=10 min (lower panel), inside a 750 nm wide nanochannel.

Figure 13:
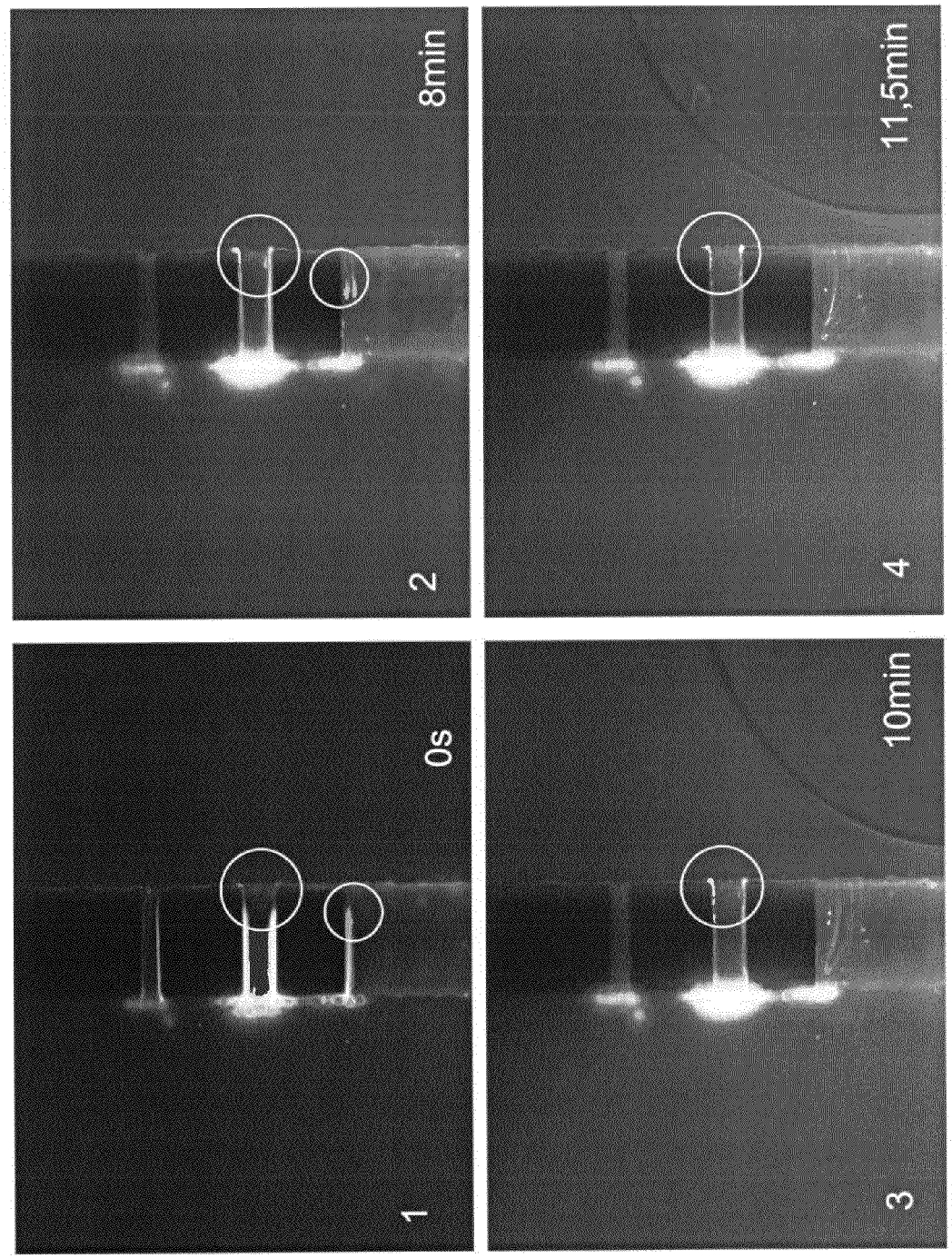

FIG. 13 shows a fluorescence image of the accumulation of digested fragments of DNA at the exit of the nanochannels (compare white circles, panels 1-4 showing different time points FIG. 14a-c shows the result of enzymatic digestion inside nanochannels with widths of 500 nm, 750 nm, 1 µm, 1.5 µm, and 2 µm. t=0 h, t=2 h, t=16 h (panels from top to bottom), respectively.

Figure 15B:
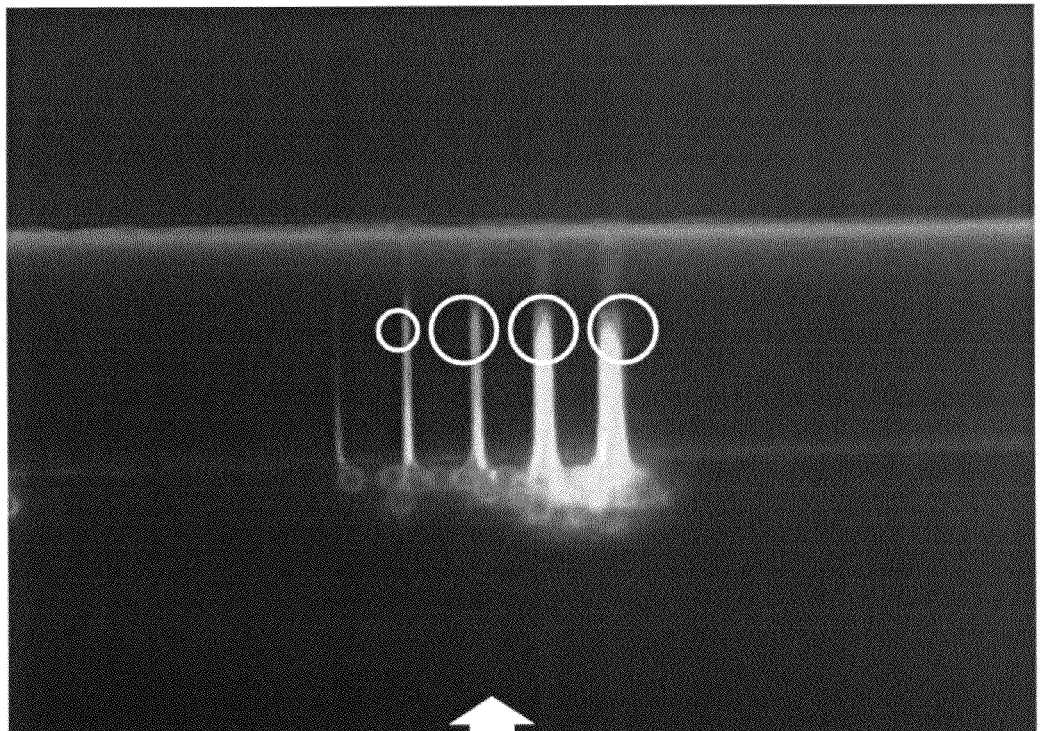
Figure 15A:
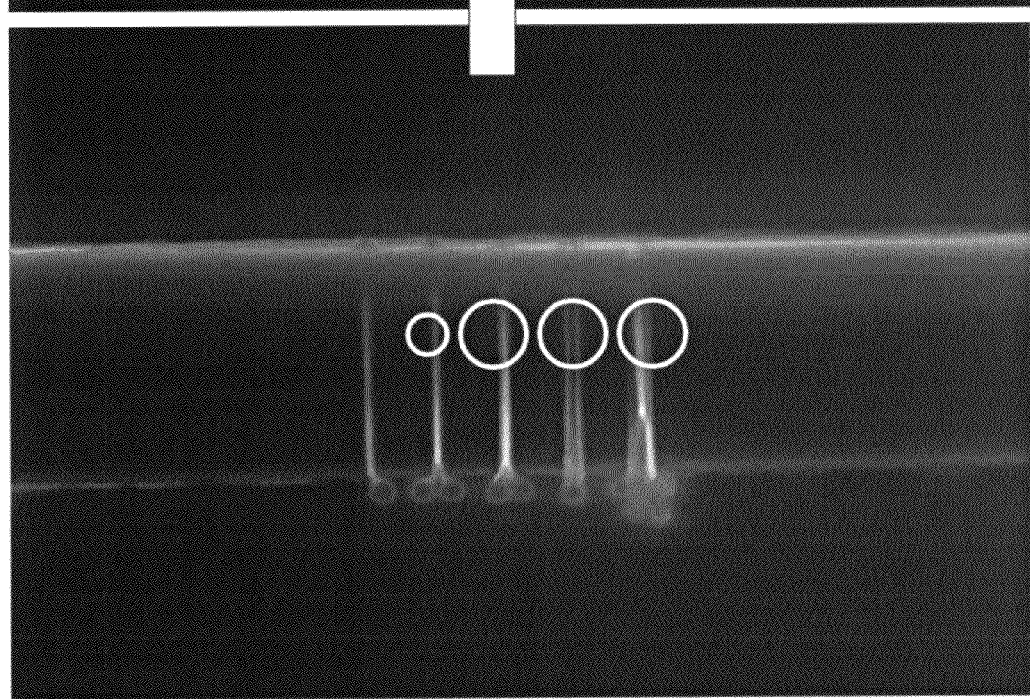

FIG. 15a and FIG. 15b show a fluorescence image of the trapping of an increased number of bead-DNA assemblies, leading to higher DNA concentration inside the nanochannel.

Figure 16B:
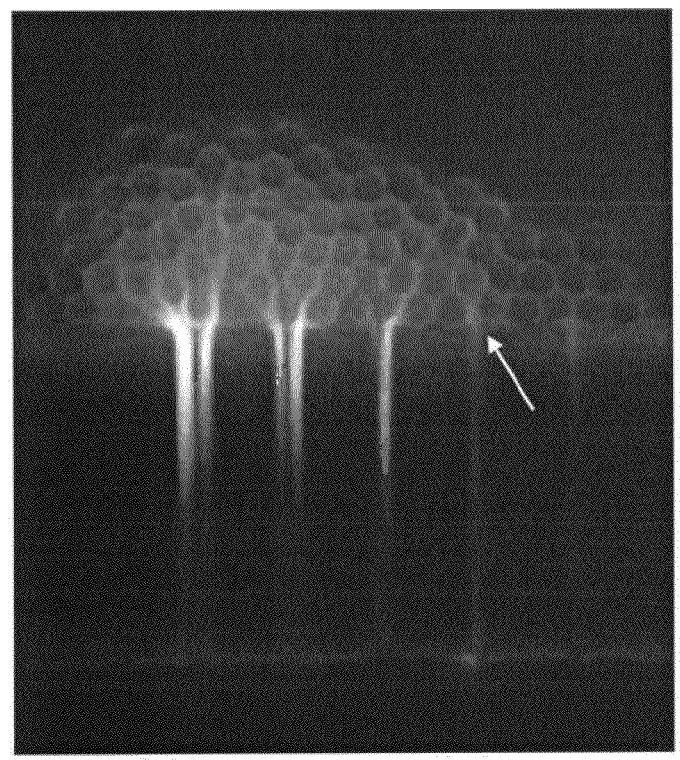
Figure 16A:
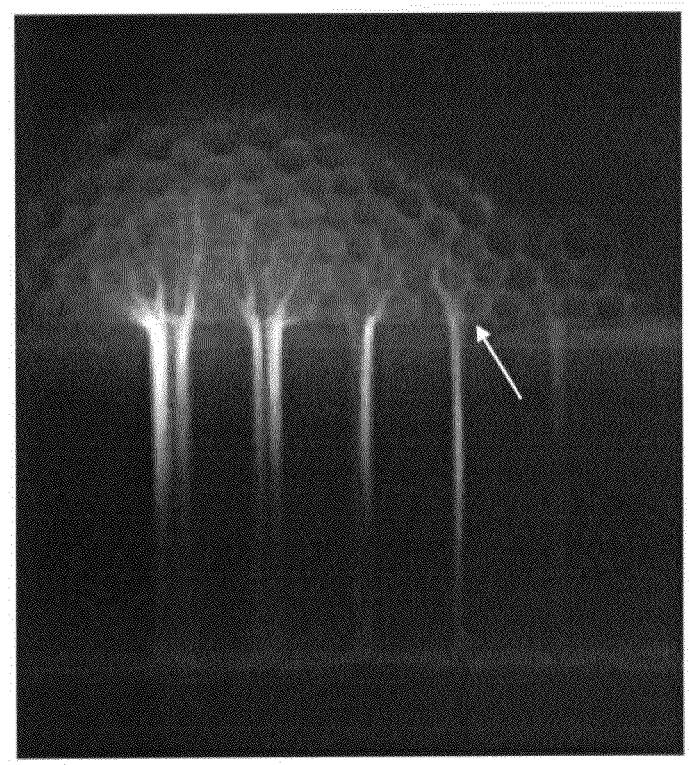

FIG. 16a and FIG. 16b show fluorescent images of the release of a single DNA strand inside the nanochannel, by using the SfO I enzyme, which cuts the DNA close to its anchor point at the bead.

Figure 17:
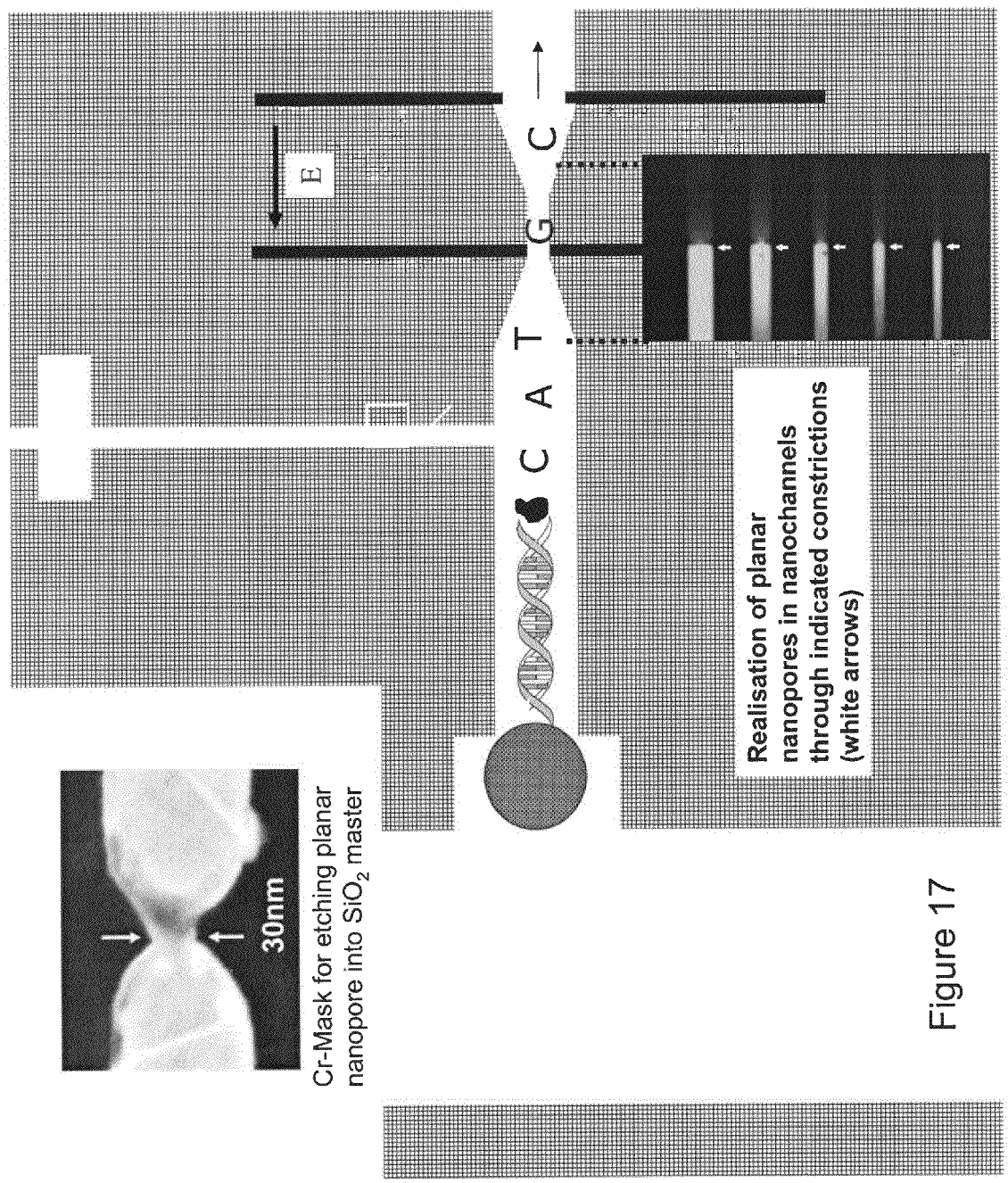

FIG. 17 shows the realisation of constrictions along the nano-channels.

The invention is now further described by reference to the following examples which are intended to illustrate, not to limit the scope of the invention.

EXAMPLE 1

DNA Sequencing

This example describes how to capture DNA molecules using polystyrene beads inside µ-fluidic structures, how to transport the bead-DNA assemblies to the point of processing, how to trap them at a desired locations, and how to finally process the DNA by using an enzyme. The enzyme releases base by base which are driven into a molecular detector and subsequently analysed.

FIG. 5a/b describes an embodiment of the device concept. After capturing a biotin-modified nucleic acid strand, e.g. a DNA strand by using a streptavidin-coated polystyrene bead, this assembly is driven (by hydrodynamic flow or electric or magnetic fields) into a microfluidic-nanofluidic transition structure (Tag 1). During this step, an enzyme (represented by a black spot) is added to the assembly, while the co-factor of the enzyme is not yet present (Tag 2). The assembly is then trapped either by an external and preferably inhomogeneous electric or magnetic field, or in a structural constriction like a micro-to-nano tapered transition (Tag 3). The nucleic acid, e.g. DNA is stretched towards the point of detection by using either hydrodynamic flow or electric fields (Tag 4). A possible extension is to attach other objects (like beads, macromolecules, proteins) to the end or the backbone to the nucleic acid, e.g. DNA in order to further support the stretching process. These objects could be accessed by magnetic or electric fields.

By adding co-factor (e.g., $Mg^{2+}$) the digestion and release of single bases is started (Tag 5). The negatively charged single bases are driven towards the molecular detector either by hydrodynamic flow or electric fields (Tag 6). The molecular detector could be one of the recently published single-molecule sensors, like protein-based nanopores (U.S. Pat. No. 6,936,433 B2)—especially, the combination of a pore-protein with a molecular adapter (Y. Astier et al., J. Am. Chem. Soc., 128, 5 (2006) 1705-1710), artificial nanopores (C. Dekker, Nature Nanotechnology 2 (2007) 209-215), and nanogap-based sensors (J. Lagerqvist et al., Nano Lett., 6, 4 (2006) 779-782; M. Zwolak and M. Di Ventra, Nano Lett., 5, 3 (2005) 421-424). The signal of each base will then be recorded and the sequence will be assembled.

In another embodiment, the nucleic acid-bead assembly, e.g. the DNA-bead assembly is trapped at the tapered micro-to-nano constriction—without having already the enzyme attached to the DNA. Then, after stretching the nucleic acid, e.g. DNA into the nanochannel, the digestion step is started by adding the enzyme and the co-factor $Mg^{2+}$.

FIG. 5c shows an embodiment wherein an enzyme for processing is immobilized on the surface of the carrier particles.

The nucleic acid digesting enzyme, e.g. DNA digesting enzyme can be bound to carrier beads via biotin-avidin linkage, Ni-chelate binding, aptamer binding, direct coupling via amine, maleimide, reduced cysteine, glutaraldehyde, or thiols, preferably with a spacer molecule between carrier and enzyme to reduce degradation of the enzyme on the carrier surface. The enzyme carrying carriers are trapped at a second constriction or by electric or magnetic fields (Tag 0). Preferably, the enzyme carrier beads are somewhat smaller than the DNA carrier beads. The DNA is inserted into the nanochannel by the same procedure as mentioned above (Tag 3) and the DNA is directed towards to location of the immobilised enzymes. As the end of the DNA approaches one enzyme, the digestion starts (Tag 4) if the co-factor is present in the solution (Tag 5) and the DNA fragments can reach the molecular detector (Tag 6).

By using auxiliary electrodes as shown in FIG. 5b it is possible to position the DNA carrier bead successively closer towards the enzyme as the digestion proceeds. It can be also envisioned to bounce the DNA carrier against the enzyme carrier once the DNA is attached to one of the enzymes, leaving the not yet processed part of the DNA relaxed as a loop.

It is also possible to release the DNA completely from the carrier bead as the digestion starts (e.g. enzymatically, by light, heat etc).

In the following the practical realisation of the concept shown in FIG. 5a is described.

FIG. 6 shows a DNA-bead assembly in solution on a glass surface.

Biotinylated oligonucleotide was hybridized to the 12-nucleotide overhang at the right (one) end of the bacteriophage lambda-DNA (48,502 base pairs (bp); Sigma). The complementary and overlapping oligonucleotide (5'-GGG-CGG-CGA-CCT-3') is phosphorylated in 5' and biotin labelled in 3' (purchased from Eurogentec). The lambda DNA was mixed with the oligonucleotide at a molar ratio of 1:1000 and allowed to hybridize at 50° C. for 1 hr, followed by ligation over night at 16° C. with DNA Ligase (Invitrogen) in ligase buffer (Invitrogen). Not hybridized excess oligomeres were removed by filtration. The purified, biotin modified DNA was stored at +4° C. in 137 mM PBS buffer (pH 7.4).

The biotinylated lambda DNA was immobilized on straptavidin coated polystyrene (PS) beads (Polyscience, Inc), which had a diameter of 1.8 µm. The ratio PS particle to DNA strand was 1:1000. The mixture was shaken in 1 M PBS buffer at low volume for 72 hr at room temperature. The DNA assemblies were stored at +4° C. in 1 M PBS buffer. Prior to use them in the micro-fluidic device the DNA was diluted 1:50 and stained with YOYO-1 (Molecular Probes) at RT for 1 h at a dye/bp ratio of 1:2 (or 1:10 if not diluted-in first experiments).

FIG. 7 a shows the schematic steps to produce a master structure (for subsequent manufacture of a monolithic substrate) and FIG. 7b shows an example of the fabricated master structure on a silicon wafer that was used for PDMS molding to realise a substrate according to the present invention having micro- and nanochannels.

A (100) Silicon wafer with 1000 nm of thermally grown oxide was covered with PMMA_MA resist at 2000 rpm. Nanostructures of various widths in the range 100 nm up to 2 µm were exposed into the PMMA by using a 50 kV ebeam writer (Step A). After development in PMMA developer for 3 minutes, a 30 nm thick Chromium layer was thermally evaporated onto the PMMA mask (Step B). After a lift-off for 6-12 hours (Step C), the wafer was etched using a reactive ion etching machine and CHF3/Ar gas mixtures for a couple of minutes to reach an etching depth between 200 and 500 nm (Step D). After a 60 s wet-chemical etching step of the Cr mask (Step E), SU8 epoxy-based, negative-tone UV resist (Microresists, Germany) was spun onto the structure at 3000 rpm (Step F), leading to a resist thickness of about 10 µm. After baking the resist at 65° C. for 2 minutes and at 95° C. for 5 minutes, the layer was UV exposed for 22 seconds, postbaked at 65° C. for 1 minute and at 95° C. for 2 minutes to produce microchannels. The developing steps were performed in SU8 developer (Microresists, Germany) for 2 minutes followed by a rinse in isopropanol (Step G). An SEM image of the resulting master structure is shown in FIG. 7b.

The master was fluoro-silanised in the gas phase using (Tridecafluoro-1,1,2,2-tetrahydro-octyl)-trichlorosilane silane, at a partial pressure of approximately 4 mbar for 45 minutes. This layer works well as an anti-sticking layer for the following molding step.

PDMS elastomer (Stygard 184, Dow Chemicals) was mixed with PDMS curing agent at a ratio 10:1, pored over the master and cured for 10 hours at 65° C. After releasing the cured PDMS from the master, the PDMS sheet was cut into pieces and holes for in- and outlets were punched. The PDMS was activated—along the glass slides—in a PlasmaLab 80 (OxfordInstruments, Germany) for 10 seconds, 120 mtorr at 70 W and an O$_2$ flow of 50 sccm.

After this, the glass slides and PDMS sheets were aligned and gently pressed together, which leads to an irreversible bond between the PDMS and the glass. In order to include electrodes into the fluidic device, microfabricated Cr/Au electrode were attached to the cover slide which closes the fluidic channels. A proper optical alignment was necessary to overlay the electrodes onto the channels.

Figure 8A:
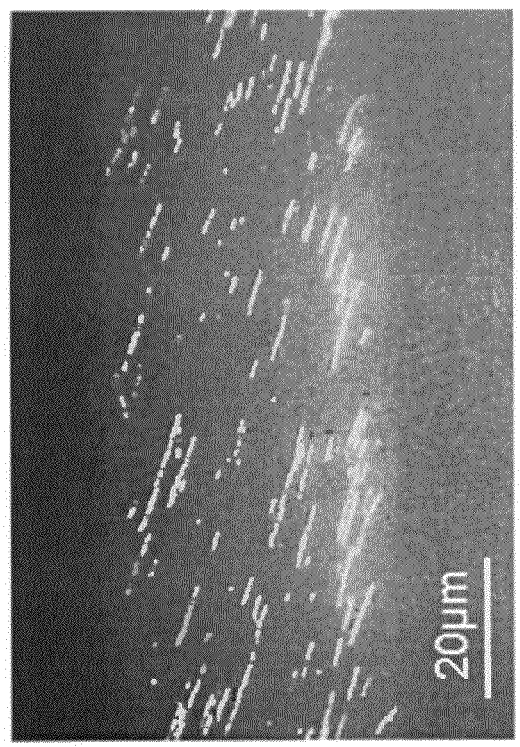
Figure 8B:
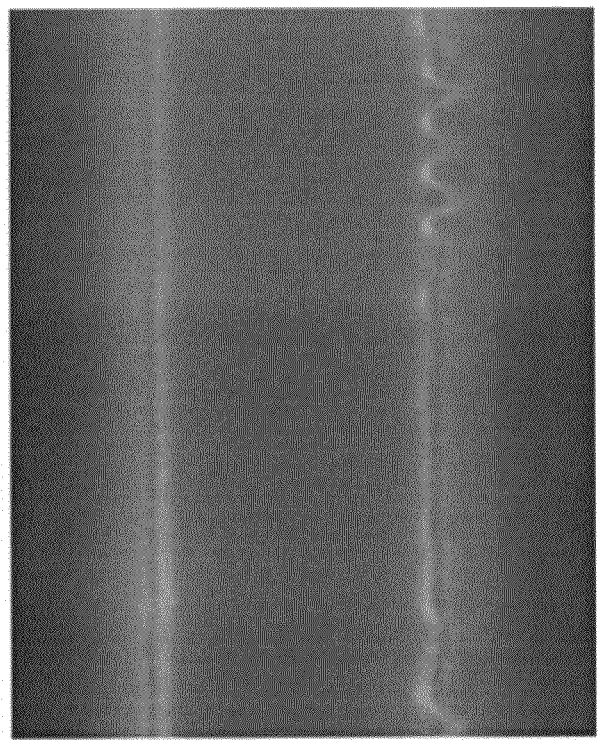

In order to reduce the non-specific adsorption of DNA molecules on the device surface, the bonded device was filled with gas of methyltriethoxysilan, which was brought into the gas phase by heating the silane solution for 30 minutes at 120° C. degree. FIG. 8a demonstrates the adsorption of DNA molecules on a freshly bonded, non-treated glass surface and FIG. 8b shows that no adsorption takes place under similar conditions, however, for the case of a methyl-silanised glass surface.

FIG. 9 shows an example of the micro-to-nano-transition and the trapping of one DNA-bead assembly. The DNA molecules get stretched into the nanofluidic channel. FIG. 10 shows the addition of one DNA-bead assembly to already trapped assemblies.

FIG. 11a and 11b show the manipulation of the trapped DNA by using electric DC fields. Here, the maximum applied DC voltage to Cr/Au overlay electrodes (microfabricated on the glass slide, which closes the microfluidic structure) was 2V, the PBS buffer concentration was 70 mM.

FIG. 11c shows the manipulation by reversed hydrodynamic flow.

FIG. 12 shows the digestion of trapped DNA using an exonuclease enzyme (Exo III), at t=0 s, t1=5 min, t2=10 min—in a 750 nm wide nanochannel.

After trapping a few bead-DNA assemblies the 1 M PBS assembly buffer was exchanged with the enzyme buffer (NEBI, New England BioLabs, New England, USA) without co-factor Mg$^{2+}$. Exonuclease III (New England BioLabs, New England, USA) was added in the concentration of 1 U/µl. In this stage no digestion is visible. After adding magnesium in a concentration of 10 mM with the enzyme buffer, all lambda DNA was digested within approximately 10 minutes.

FIG. 13 shows the accumulation of digested fragments of DNA at the exit of the nanochannels—the molecular detector should be installed at such location (compare white circles).

The realisation of a planar nanopore detector is shown in FIG. 17. The inset shows the SEM image of a 30 nm constriction in a Cr mask, which is used to define the nanochannel structure in the SiO$_2$ master (Step C and D in FIG. 7a). After PDMS molding and bonding to glass, the inventors could verify that such small constrictions could be transferred into the PDMS structure and could still be filled with an aqueous solution, which contains the FITC dye (FIG. 17). In this concept, a temporal blockage of the constriction by a translocating object could be measured by monitoring the ionic current through the constriction.

After these steps, the used and empty carrier bead can be released from the micro/nano-transition by for example applying an electric, magnetic field, mechanical vibrations or by reversed hydrodynamic flow (FIG. 11c).

EXAMPLE 2

Influence of Structure Sizes on Enzymatic Activity

The present inventors have observed that the DNA digestion process seems to be more efficient in wider channels than in very narrow channels. 14a-c shows the result of a DNA digestion experiment using the Xba enzyme (New England BioLabs, New England, USA) on trapped DNA molecules. FIG. 14a shows the situation at t=0, then after adding Xba I it cleaves λ-DNA at about the center position (24508 bp). One can clearly see that after 2 h the digestion has well proceeded in the wider channels, i.e. >1 μm (FIG. 14b), while almost no change has happed in the narrow channels (≤1 μm). FIG. 14c shows the situation 16 h later, where almost all DNA strands show the same length, suggesting that the digestion activity was considerably lower the narrow channels. Obviously, Xba I is more sensitive against spatial confinements.

The inventors have repeatedly seen, that the DNA molecules in the narrow channels remain longer after the enzymatic digestion step and conclude that careful structural control of the channel dimensions could be use to adjust the enzymatic activity.

EXAMPLE 3

Molecule Pre-Concentration and Transport to the Point of Detection in Liquid Phase In this example we demonstrate that the concentration of DNA molecules can be increased locally through the trapping of more than one carrier in the vicinity of a micro-to-nano transition. FIG. 15a shows just a few bead-DNA assemblies trapped at the micro-to-nano transition, leading to a certain fluorescence intensity in the nanochannel. FIG. 15b shows the same channel a few moments later. More beads are trapped, leading to a higher local concentration of DNA—as it can be concluded from the stronger fluorescence.

EXAMPLE 4

Release of Analyte (DNA) from Bead by Using an Enzyme

In this example the present inventors demonstate the complete release of the DNA molecule, after the bead-DNA assemblies are being trapped in the vicinity of a micro-to-nano transition. Here, the Sfo I enzyme (New England BioLabs, New England, USA) was used, which cuts the lambda DNA close to the anchor point to the bead. FIG. 16a shows the initially trapped bead-DNA assemblies—FIG. 16b shows the same spot after the enzyme-initiated release of a DNA strand in one channel as marked by the arrows.

The features of the present invention disclosed in the specification, the claims and/or in the accompanying drawings, may, both separately, and in any combination thereof, be material for realizing the invention in various forms thereof.

The invention claimed is:

1. A device for processing an analyte, wherein said device comprises:
    a substrate, wherein said substrate is a monolithic piece of material and comprises:
        a system of channels comprising:
            at least a first channel, said first channel having dimensions of from 1 μm to 1 mm in depth and width, and
            at least a second channel, said second channel being in fluid connection with said first channel and having dimensions of from 1 nm to 2000 nm in depth and width, said first channel flowing into said second channel,
        wherein the second channel is smaller than the first channel;
        a region of analyte processing or release formed at a position where said first channel flows into said second channel;
        a detector being in fluid connection with said second channel and being spaced apart from said region of analyte processing or release, wherein said detector is selected from the group consisting of a biological pore protein, an artificial nanopore and a nanogap sensor;
        a carrier particle capable of binding the analyte;
        a solvent within said system of channels capable of transporting said carrier particle within said first channel; and
        a separate channel connected to said second channel comprising a co-factor for adding the co-factor to an enzyme and the analyte,
    wherein the first channel comprises the carrier particles bound to the analyte and the enzyme, and the second channel comprises an analyte processed or released by activating the bound enzyme with the co-factor, and
    wherein said substrate is made of a polymer or a combination of polymers, and said substrate is formed as a monolithic piece of material by molding or embossing said polymer or combination of polymers using a master.

2. The device according to claim 1, wherein said substrate is not a composite substrate.

3. The device according to claim 1, wherein said carrier particle has a size of from 0.1 nm to 1 mm.

4. The device according to claim 1, wherein said first channel has dimensions at least 5 times wider and deeper than a size of said carrier particle.

5. The device according to claim 1, wherein said first channel has dimensions of from 10 μm to 20 μm in depth and from 10 μm to 200 μm in width, and said carrier particle has a size of ≤2 μm.

6. The device according to claim 1, wherein said region of analyte processing or release has a tapered structure wherein a cross-section of said system of channels decreases in discrete steps from said first channel to said second channel.

7. The device according to claim 1, wherein said second channel has dimensions of from 100 nm to 800 nm in depth and width.

8. The device according to claim 1, wherein said second channel has dimensions of from >1 μm to 2 μm.

9. The device according to claim 1, wherein said first channel further comprises a structure of hindrance preventing an unhindered flow of said solvent and said carrier particle in said first channel.

10. The device according to claim 9, wherein said structure of hindrance comprises one or more squares, rectangles and circles of matter arranged in said first channel.

11. The device according to claim 1, wherein said carrier particle comprises one or more carrier particles that are spherical, cubical, paralleliped or irregular in shape.

12. The device according to claim 1, wherein said first channel has a length of from 1 mm to 10 cm, and said second channel has a length of from 1 nm to 1 mm.

13. The device according to claim 1, wherein said detector is at a distance from said region of analyte processing or release of from 1 nm to 1000 μm.

14. The device according to claim 1, further comprising a means for introducing and/or maintaining a flow of solvent and carrier particle through said system of channels.

15. The device according to claim 14, wherein said means for introducing and/or maintaining a flow of solvent and carrier particle through said system of channels involves exerting a force on said solvent and/or said carrier particle, wherein said force is selected from the group consisting of an electric force, a magnetic force, an electromagnetic force and a hydrodynamic force.

16. The device according to claim 1, further comprising a means for immobilizing said carrier particle at said region of analyte processing or release.

17. The device according to claim 16, wherein said means for immobilizing said carrier particle at said region of analyte processing or release involves exerting a force on said solvent and/or said carrier particle, wherein said force is selected from the group consisting of an electric force, a magnetic force, an electromagnetic force and a hydrodynamic forces force.

18. The device according to claim 1, wherein said polymer is at least one selected from the group consisting of PDMS, polycarbonate and PE.

19. The device according to claim 1, wherein said carrier particle is made of a material selected from the group consisting of silicon oxide, $Al_2O_3$, a metallic and/or magnetic material, Au, Ag, Pd, Pt, Al, Ti, Fe, Ni, a ceramic, a polymer, polymethylmethacrylate (PMMA), polystyrene, teflon, malamine, polylactide and dextran.

20. The device according to claim 1, wherein said carrier particle further comprises an analyte-binding group which interacts with a corresponding carrier particle-binding group on said analyte.

21. The device according to claim 20, wherein a pair of analyte-binding group and corresponding carrier particle-binding group is selected from the group consisting of biotin/(strept)avidin, antibody/antigen, gold/thiol modifications, Nickel/$His_6$, lectine/sugar, glutathione/glutathione-S-transferase, $NH_2$/COOH/epoxy covalent binding, Protein A, G binding with high affinity to the $F_c$ portion of various classes and subclasses of immunoglobulins from a variety of species, hydrogen bonds, DNA-base hybridisation, aptamer binding, protein-DNA/RNA interaction, collagen/collagen-binding proteins, Dig/anti-digoxigenin, hormone binding, electrostatic, ionic, and covalent interactions.

22. The device according to claim 1, wherein said system of channels is modified at a surface of said channels by application of a chemical species to reduce a non-specific adsorption of said analyte on the surface of said channels.

23. The device according to claim 22, wherein said modification is performed through liquid phase deposition or gas phase deposition of a silane.

24. The device according to claim 22, wherein said surface of said channels is selected from the group consisting of a polymer and silicon oxide.

25. The device according to claim 24, wherein said modification is performed by exposing said surface to silane compounds having a chemical endgroup selected from the group consisting of a methyl group, an amino group, a fluoro group, a thiol group, and a molecular specie that exposes a hydrophobic group to said surface of said channels.

26. The device according to claim 1, further comprising a means for releasing said analyte from said carrier particle at said region of analyte processing or release.

27. The device according to claim 26, wherein said means for releasing said analyte from said carrier particle at said region of analyte processing or release is selected from the group consisting of a photoinduced release, an electric field-induced release, a temperature-induced release, a chemical reaction release and a biochemical reaction release with an optional co-factor or enzyme mediated-induced release.

28. The device according to claim 1, further comprising a means for further processing said analyte by a chemical reaction and cleavage into smaller fragments or building blocks.

29. The device according to claim 28, wherein said means for further processing said analyte by said chemical reaction is a carrier bead on which a chemical agent or an enzyme is immobilized.

30. The device according to claim 1, wherein said analyte is selected from the group consisting of a single stranded nucleic acid, a double stranded nucleic acid, DNA, RNA, a protein, a polypeptide, a drug, a molecule that is in a liquid phase under ambient conditions, a molecule that is in a gas phase under ambient conditions, a biologically hazardous molecule, and an environmentally hazardous molecule.

31. The device according to claim 1, wherein said detector is said biological pore protein.

32. The device according to claim 1, wherein said detector is said artificial nanopore.

33. The device according to claim 1, wherein said detector is said nanogap sensor.

34. The device according to claim 1, wherein the analyte is a nucleic acid and said separate channel comprises a co-factor for adding the co-factor to an enzyme and the nucleic acid and for controlling nucleic acid digestion and release of single bases.

35. The device according to claim 1, wherein the co-factor is $Mg^{2+}$ ions.

36. The device according to claim 1, wherein said region of analyte processing or release has a tapered structure wherein a cross-section of said system of channels decreases continuously from said first channel to said second channel.

37. A method of processing and/or detecting an analyte, wherein said method comprises:
  binding an analyte to a carrier particle capable of binding to the analyte; transporting said carrier particle and analyte bound thereto through said system of channels of said device according to claim 1 to said region of analyte processing or release;
  immobilizing said carrier particle and analyte bound thereto at said region of analyte processing or release;
  releasing and/or processing said analyte by applying a light, an electrical field, a magnetic field, an electromagnetic field, heat or cold, and/or by performing a reaction with said enzyme selected from the group consisting of a nuclease, a protease, Exo I, Exo III, Sfo I, Xba I and a restriction enzyme, to obtain a released analyte and/or a processed analyte;
  transporting said released analyte and/or said processed analyte to said detector; and
  detecting said released analyte and/or said processed analyte with said detector.

38. The method according to claim 37, further comprising removing said carrier particle from said region of analyte processing or release after said analyte has been released and/or processed.

39. The method according to claim 37, wherein said transporting and said removing comprise introducing and/or maintaining a flow of said solvent and said carrier particle.

40. The method according to claim 37, wherein said immobilizing is achieved by the dimensions of said region of analyte processing or release or by exerting a force on said solvent and/or said carrier particle, wherein said force is selected from the group consisting of an electric force, a magnetic force, an electromagnetic force and a hydrodynamic forces force, or by a combination of both.

41. The method according to claim 37, wherein said detecting said released analyte and/or said processed analyte with said detector occurs by a detection selected from the group consisting of optical detection, chemical detection, electrical detection, magnetic detection, and electrochemical detection.

42. The method according to claim 37, wherein said analyte is a nucleic acid, said processing said analyte is by an enzymatic degradation of said nucleic acid, and said detecting said processed analyte includes detection of a nucleotide to elucidate the sequence of said nucleic acid.

43. The method according to claim 42, wherein said enzymatic degradation is performed by adding a carrier bead into said system of channels, wherein an enzyme for said enzymatic degradation has been immobilized on said carrier bead.

44. A device for processing an analyte, wherein said device comprises:
a substrate, wherein said substrate is a monolithic piece of material and comprises:
a system of channels comprising:
at least a first channel, said first channel having dimensions of from 1 μm to 1 mm in depth and width, and
at least a second channel, said second channel being in fluid connection with said first channel and having dimensions of from 1 nm to 2000 nm in depth and width, said first channel flowing into said second channel,
wherein the second channel is smaller than the first channel;
a region of analyte processing or release formed at a position where said first channel flows into said second channel;
a detector being in fluid connection with said second channel and being spaced apart from said region of analyte processing or release, wherein said detector is selected from the group consisting of a biological pore protein, an artificial nanopore and a nanogap sensor; and
a separate channel connected to the second channel comprising a co-factor for adding the co-factor to an enzyme and the analyte,
wherein the first channel comprises the carrier particles bound to the analyte and the enzyme, and the second channel comprises an analyte processed or released by activating the bound enzyme with the co-factor, and
wherein said substrate is made of a polymer or a combination of polymers, and said substrate is formed as a monolithic piece of material by molding or embossing said polymer or combination of polymers using a master.

45. The device according to claim 44, wherein the analyte is a nucleic acid and said separate channel comprises a co-factor for adding the co-factor to an enzyme and the nucleic acid and for controlling nucleic acid digestion and release of single bases.

* * * * *